(12) United States Patent
Rao et al.

(10) Patent No.: US 6,403,814 B1
(45) Date of Patent: Jun. 11, 2002

(54) METHOD FOR SYNTHESIZING DIARYL-SUBSTITUTED HETEROCYCLIC COMPOUNDS, INCLUDING TETRAHYDROFURANS

(75) Inventors: Alla Venkata Rama Rao, Hyderabad (IN); Mukund S. Chorghade, Natick, MA (US); Amin ul Islam, Hyderabad (IN); Vemuri Venkata Kiran Rao, Hyderabad (IN); Anegondi Sreenivasa Prasad, Hyderabad (IN); Batchu Venkateswara Rao, Nellore (IN); Ranga Reddy, Andhra Pradesh (IN); Lalata Krishnakanth Reddy, Andhra Pradesh (IN); Kotakonda Shailaja, Andhra Pradesh (IN); Mukund Keshao Gurjar, Pune (IN); Sunil Vyankatesh Mhaskar, Natick, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/418,637

(22) Filed: Oct. 15, 1999

Related U.S. Application Data

(63) Continuation of application No. 09/173,918, filed on Oct. 16, 1998, now Pat. No. 6,255,498.

(51) Int. Cl.$^7$ ............................................. C07D 307/02
(52) U.S. Cl. ....................................................... 549/475
(58) Field of Search .......................................... 549/475

(56) References Cited

U.S. PATENT DOCUMENTS

| | | | |
|---|---|---|---|
| 5,037,853 A | 8/1991 | Brooks et al. | 514/595 |
| 5,112,848 A | 5/1992 | Brooks et al. | 514/424 |
| 5,169,854 A | 12/1992 | Brooks et al. | 514/314 |
| 5,175,183 A | 12/1992 | Brooks et al. | 514/438 |
| 5,183,818 A | 2/1993 | Brooks et al. | 514/231.5 |
| 5,187,192 A | 2/1993 | Brooks et al. | 514/445 |
| 5,288,751 A | 2/1994 | Brooks et al. | 514/438 |
| 5,326,787 A | 7/1994 | Brooks et al. | 514/507 |
| 5,358,938 A | 10/1994 | Cai et al. | 514/231.5 |
| 5,434,151 A | 7/1995 | Cai et al. | 514/231.5 |
| 5,463,083 A | 10/1995 | Biftu et al. | 549/71 |
| 5,530,141 A | 6/1996 | Shen et al. | 549/39 |
| 5,543,531 A | 8/1996 | Funfschilling et al. | |
| 5,639,782 A | 6/1997 | Shen et al. | 574/440 |
| 5,681,966 A | 10/1997 | Cai et al. | 549/65 |
| 5,703,093 A | 12/1997 | Cai et al. | 514/473 |
| 5,741,809 A | 4/1998 | Biftu et al. | 514/428 |
| 5,750,565 A | 5/1998 | Cai et al. | 514/473 |
| 5,756,768 A | 5/1998 | Kanou et al. | |
| 5,780,503 A | 7/1998 | Biftu et al. | 514/471 |
| 5,792,776 A | 8/1998 | Biftu et al. | 514/303 |
| 5,856,323 A | 1/1999 | Cai et al. | 514/231.5 |

FOREIGN PATENT DOCUMENTS

| | | |
|---|---|---|
| WO | WO 92/15294 | 9/1992 |
| WO | WO 94/01430 | 1/1994 |
| WO | WO 94/06790 | 3/1994 |
| WO | Wo 95/18610 | 7/1995 |
| WO | WO 96/00212 | 1/1996 |

*Primary Examiner*—Amelia Owens
(74) *Attorney, Agent, or Firm*—Peter F. Corless; Edwards & Angell, LLP

(57) ABSTRACT

A method is provided for synthesizing diaryl-substituted heterocyclic compounds, particularly 2,5-diaryl-substituted tetrahydrofurans and tetrahydrothiophenes. Methods for synthesizing starting materials and intermediates are provided as well. An important application of the invention is in the synthesis of CMI-392, (±)trans-2-[5-N'-methyl-N'-hydroxyureidyl-methyl)3-methoxy-4-p-chlorophenylthioethoxyphenyl]-5-(3,4,5-trimethoxyphenyl)-tetrahydrofuran, a highly effective agent in treating inflammatory and immune disorders. The invention also encompasses novel compounds useful as starting materials and intermediates in the synthetic processes disclosed.

8 Claims, 6 Drawing Sheets

112

113

114

115 (crude CMI-392)

isopropanol/
n-hexane 116 (pure crystalline CMI-392)

METHOD FOR SYNTHESIZING DIARYL-SUBSTITUTED HETEROCYCLIC COMPOUNDS, INCLUDING TETRAHYDROFURANS

CROSS-REFERENCE TO RELATED APPLICATION

The present application is a continuation of U.S. provisional application originally having application Ser. No. 09/173,918, filed Oct. 16, 1998, now U.S. Pat. No. 6,255,498 incorporated herein by reference in its entirety.

TECHNICAL FIELD

The present invention relates generally to the field of synthetic organic chemistry, and more particularly relates to a novel method for synthesizing diaryl-substituted heterocyclic compounds useful for treating inflammatory and immune disorders. The invention also pertains to novel chemical compounds useful as intermediates in the presently disclosed synthetic methods.

BACKGROUND

Allergy, asthma, autoimmune disorders and tissue injury are known to induce the release of lipid mediators, leukotrienes generated by the 5-lipoxygenase ("5-LO") pathway, and platelet activating factor ("PAF"; 1-O-alkyl-2-acetyl-sn-glycerol-3-phosphoryl choline) from leukocytes. Leukotrienes and PAF trigger the major symptoms of inflammatory diseases: bronchoconstriction, cellular infiltration, swelling, congestion and pain. Recent efforts in identifying and developing effective agents to treat inflammatory and immune disorders have led to the synthesis of a family of important compounds, described in detail in U.S. Pat. No. 5,434,151 to Cai et al. Those compounds reduce damage arising from an inflammatory or immune response by acting as receptor antagonists of platelet activating factor by inhibiting the activity of 5-lipoxygenase, or both. As described in detail in the aforementioned patent, the compounds are 2,5-diaryl tetrahydrothiophenes, tetrahydrofurans, and pyrrolidines, 1,3-diaryl cyclopentanes, and 2,4-diaryl tetrahydrothiophenes, tetrahydrofurans and pyrrolidines. An exemplary compound is (±)trans-2-[5-(N'-methyl-N'-hydroxyureidylmethyl)-3-methoxy-4-p-chloro-phenylthioethoxy-phenyl]-5-(3,4,5-trimethoxyphenyl) tetrahydrofuran, sometimes referred to herein as "CMI-392" and shown in the following formula:

CMI-392

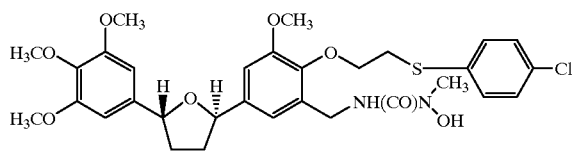

CMI-392, a compound that, uniquely, is both a 5-LO inhibitor and a PAF receptor antagonist, has proved to be an extremely effective agent for treating inflammatory and immune disorders, as have the other compounds set forth in the Cai et al. patent. The compounds have been found to be particularly useful in treating psoriasis and atopic dermatitis, both chronic inflammatory skin disorders affecting millions of people. A number of pharmaceutical compositions containing these drugs have been proposed and prepared. However, there remains a need for an improved synthetic route to prepare these valuable agents.

Previously, the only known process for synthesizing and purifying CMI-392—as disclosed in U.S. Pat. No. 5,434,151 to Cai et al.—resulted in a waxy, low melting point solid that proved to be difficult to work with and sensitive to heat, light and moisture. In co-pending provisional patent application Ser. No. 09/173903, entitled "Topical Pharmaceutical Formulations Useful to Treat Inflammatory and Immune Disorders," filed on even date herewith, a method is disclosed for preparing CMI-392 and analogs thereof in a crystalline form that is stable to heat, light and moisture. That method, which involves recrystallization in isopropyl alcohol, optionally combined with n-hexane, is extraordinarily valuable insofar as a variety of different types of pharmaceutical formulations may now be prepared, aqueous vehicles may be used, and far fewer precautions need to be taken with respect to possible exposure to slightly elevated temperatures and light. Nevertheless, there remains a need for an improved synthetic route to CMI-392 and analogs thereof, preferably in crystalline form, which avoids harsh reagents and extreme reaction conditions, and provides the desired product in high yield. The present invention is directed to such a synthesis.

SUMMARY OF THE INVENTION

Accordingly, it is a primary object of the invention to address the above-mentioned need in the art by providing a new method for synthesizing CMI-392 and other diaryl-substituted heterocycles, particularly 2,5-diaryl-substituted tetrahydrofurans and 2,5-diaryl-substituted tetrahydrothiophenes.

It is another object of the invention to provide methods for synthesizing starting materials and intermediates useful for preparing diaryl-substituted heterocycles such as 2,5-diaryl-substituted tetrahydrofurans and tetrahydrothiophenes.

It is still another object of the invention to provide novel compounds useful as starting materials and/or intermediates in the synthesis of diaryl-substituted heterocycles such as 2,5-diaryl-substituted tetrahydrofurans and 2,5-diaryl-substituted tetrahydrothiophenes.

The invention also provides additional methods of synthesis that are useful for preparing diaryl-substituted heterocycles such as 2,5-diaryl-substituted tetrahydrofurans, particularly optically active substituted tetrahydrofurans, such as optically active trans-2-[3-(3-N$^1$-butyl-N$^1$-hydroxyureidyl)propoxy)-4-propoxy-5-propylsulfonyl phenyl]-5-(3,4,5-trimethoxy phenyl) tetrahydrofuran (sometimes referred to herein as CMI-546), and optically active trans-2-[3-(3-(N$^1$-butyl-N$^1$-hydroxyureidyl) propoxy)-4-propoxy-5-methylsulfonyl phenyl]-5-(3,4,5-trimethoxy phenyl) tetrahydrofuran (sometimes referred to herein as CMI-568).

Additional objects, advantages and novel features of the invention will be set forth in part in the description which follows, and in part will become apparent to hose skilled in the art upon examination of the following, or may be learned by practice of the invention.

DETAILED DESCRIPTION OF THE INVENTION

Figure 1A:
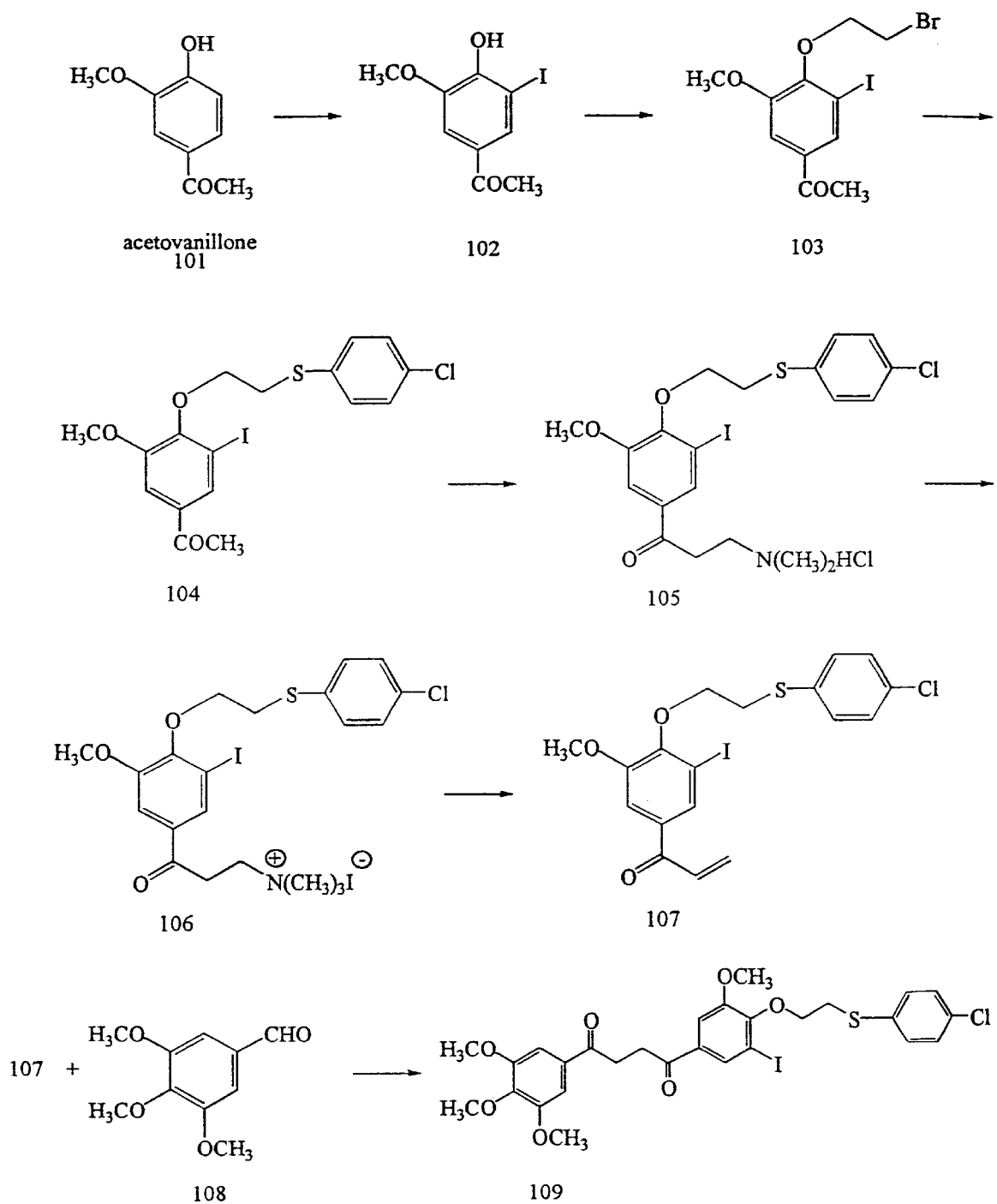
FIGS. 1a–1c schematically illustrate a method for synthesizing crystalline CMI-392 using acetovanillone as a starting material, as described in the Example.

Before the present invention is disclosed and described in detail, it is to be understood that this invention is not limited to specific starting materials, reagents, reaction conditions, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an active agent" includes mixtures of active agents, reference to "a solvent" includes mixtures of two or more solvents, and the like.

With respect to the description of chemical structures and substituents contained therein, the following definitions are applicable:

The term "alkyl" as used herein, unless otherwise specified, refers to a saturated straight chain, branched or cyclic hydrocarbon group of 1 to 10 carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term "alkenyl" as used herein, unless otherwise specified, refers to a branched, unbranched or cyclic (in the case of $C_5$ and $C_6$) hydrocarbon group of 2 to 10 carbon atoms containing at least one double bond, such as ethenyl, vinyl, allyl, octenyl, decenyl, and the like. The term "lower alkenyl" intends an alkenyl group of two to six carbon atoms, and specifically includes vinyl and allyl.

The term "alkynyl" as used herein, unless otherwise specified, refers to a branched or unbranched hydrocarbon group of 2 to 10 carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to six carbon atoms, and includes, for example, acetylenyl and propynyl.

The term "lower alkylamino" as used herein, and unless otherwise specified, refers to an amino group that has one or two lower alkyl substituents.

The term "aryl" as used herein, and unless otherwise specified, refers to phenyl or substituted phenyl, preferably wherein the substituent is halo or lower alkyl.

The term "halo" is used in its conventional sense to refer to a chloro, bromo, fluoro or iodo substituent; The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The terms "heterocycle" or "heteroaromatic," as used herein, and unless otherwise specified, refer to an aromatic moiety that includes at least one sulfur, oxygen or nitrogen atom in the aromatic ring. Such moieties include, but are not limited to, pyrryl, furyl, pyridyl, 2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl and isoxazolyl.

The term "aralkyl" refers to an aryl group with an alkyl substituent.

The term "alkaryl" refers to an alkyl group that has an aryl substituent.

The term "carbocyclic aryl" refers to an aromatic compound having 6 or more aromatic carbons without hetero aromatic ring members, typically 6 to about 18 aromatic ring members, such as phenyl, naphthyl, acenaphthyl and the like.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

As discussed herein, certain substituent groups of identified compounds may be optionally substituted. Suitable groups that may be present on such a "substituted" group include e.g. halogen (such as F, Cl, Br, or I); cyano, hydroxyl; nitro; azido; sulfhydryl; alkanoyl e.g. $C_{1-6}$ alkanoyl such as acetyl and the like; carboxamido; $C_{1-6}$ alkyl; $C_{1-6}$ alkoxy; $C_{1-6}$ alkylamino; $C_{1-6}$ alkylthio; $C_{1-6}$ alkylsulfinyl; $C_{1-6}$ alkylsulfonyl; or a heteroaromatic or heteroalicyclic group having 1 to 3 separate or fused rings with 3 to 8 members per ring and one or more N, O or S atoms e.g. courmarinyl, quinolinyl, pyridyl, pyrazonyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

In a first embodiment of the invention, a method is provided for synthesizing a diaryl-substituted heterocyclic compound, particularly a diaryl-substituted tetrahydrofuran or tetrahydrothiophene, from an aromatic aldehyde or thioaldehyde and an aromatic vinyl ketone or thioketone. The synthetic method is straightforward, makes use of mild reagents and reaction conditions, and provides the desired product in a relatively high yield. CMI-392 and analogs thereof may be synthesized, in isomerically pure form, using the presently disclosed and claimed methodology.

In a first embodiment, then, a method is provided for synthesizing a compound having the structural formula (I)

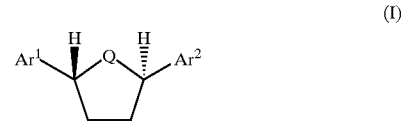

(I)

in which Q is O or S and $Ar^1$ and $Ar^2$ are selected from the group consisting of aryl, aralkyl, heteroaryl and heteroaralkyl, optionally substituted with 1 to 3 substituents. Preferably, $Ar^1$ and $Ar^2$ are independently selected from the group consisting of phenyl and pyridinyl, either unsubstituted or substituted at least one substituent selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl, m is 1, 2 or 3, and n is an integer in the range of 1 to 6. The method comprises catalytically coupling the aldehyde or thioaldehyde (II)

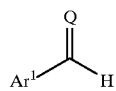

(II)

to the vinyl ketone or thioketone (III)

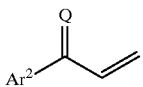

(III)

under reaction conditions effective to produce the diaryl-substituted dione or dithione

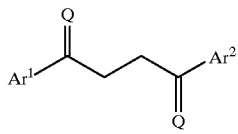

(IV)

The reaction involves admixing reactants (II) and (III) in a suitable solvent, dimethyl formamide (DMF) or the like, along with a catalyst and an organic base, preferably a tri(lower alkyl) amine such as triethylamine. The catalyst is selected so as to ensure that the coupling of the aldehyde or thioaldehyde moiety to the vinyl ketone or thioketone proceeds as desired; an exemplary catalyst is 3-benzyl-5-(2-hydroxyethyl)-4-methylthioazolium chloride. The reaction mixture is heated, preferably to at least about 50 C, more preferably to a temperature in the range of approximately 70 C to 80 C, and the reaction is allowed to proceed. After cooling to room temperature, the reaction mixture is acidified with an inorganic acid such as hydrochloric acid. The product is then isolated; typically, the acidification step results in precipitation of the desired product (IV). This coupling reaction is exemplified in part (g) of the Example herein.

In the next step, the dione or dithione (IV) is reduced with a suitable reducing agent to give the diol or dithiol (V):

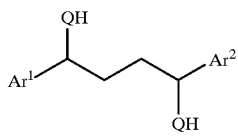

(V)

The reducing agent used to effect this reaction is, as will be appreciated by those skilled in the art, a compound which serves as a hydride donor, typically a metal hydride such as lithium aluminum hydride or sodium borohydride, with the latter agent preferred; see part (h) of the Example herein. The reaction is typically carried out in methanol, ethanol, or the like, and the reaction product may be used in the next step without purification.

Compound (V) is then caused to cyclize, to yield compound (VI):

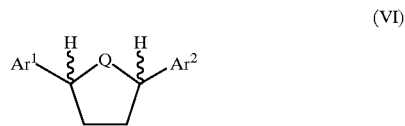

(VI)

The cyclization reaction is effected by heating the diol or dithiol (V), so that the reaction takes place at reflux. The reagents and conditions used are those which are typically used in the formation of cyclic ethers from diols; see, e.g., Schmoyer et al. (1960) *Nature* 187:592, which describes the preparation of tetrahydrofuran from 1,4-butanediol. As described in part (i) of the Example herein, the reaction may be carried out by admixing a solution of diol or dithiol (V) in benzene with orthophosphoric acid, heating to reflux, allowing the reaction to proceed to completion, and isolating the product from the organic solvent using conventional washing and extraction techniques.

The preceding step provides compound (VI) as a racemic mixture of cis and trans isomers. The racemate is then converted to the all-trans compound (I) by dissolving the racemate in a crystallization solvent, seeding the solvent with trans isomer, and cooling the mixture to promote crystallization. A particularly preferred crystallization solvent for this step is n-hexane.

In an important variation on this basic synthesis, either or both of the aromatic groups $Ar^1$ and $Ar^2$ are modified following cyclization and/or cis-trans isomerization. That is, in another embodiment of the invention, a process is provided for synthesizing a compound having the structural formula (Ia)

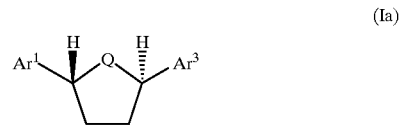

(Ia)

in which Q is O or S, $Ar^1$ is as defined above, and $Ar^3$ is as defined for $Ar^1$, the process comprising catalytically coupling an aldehyde or thioaldehyde (II)

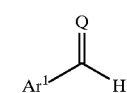

(II)

to the vinyl ketone or thioketone (III)

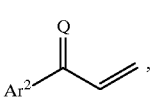

(III)

as described above, reducing the dione or dithione intermediate (IV) so provided to give the corresponding diol or dithiol (V), effecting cyclization to give the diaryl-substituted tetrahydrofuran or tetrahydrothiophene (VI)

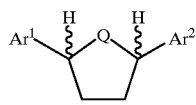

(VI)

as a racemic mixture of cis and trans isomers, chemically modifying Ar² to give Ar³, thus providing compound (VIa)

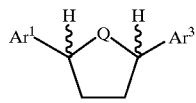

(VIa)

as a racemic mixture of cis and trans isomers, and effecting cis-trans isomerization in a suitable crystallization solvent, as explained above. Alternatively, Ar² may be converted to Ar³ following cis-trans isomerization.

Preferably, in this embodiment, Ar¹ is

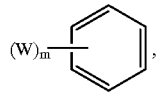

Ar² is

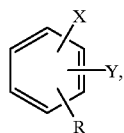

and Ar³ is

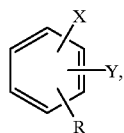

so that compound (Ia) is

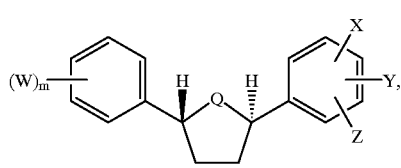

wherein:
the W are independently selected from the group consisting of alkyl, alkenyl, alkynyl, halogen, halogenated alkyl, halogenated alkenyl, halogenated alkynyl, —OR¹, —(CH₂)ₙOR¹, —O(CH₂)ₙOR¹, —SR¹, —(CH₂)ₙSR¹, —S(CH₂)ₙSR¹, —COOR¹, —(CO)R¹, —NR²R³, —(CO)NR²R³, —O(CO)NR²R³, and —CN, wherein R¹, R² and R³ are independently hydrogen, alkyl or aryl, m is 1, 2 or 3, and n is an integer in the range of 1 to 6;
X is defined as for W;

Y is

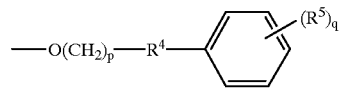

in which p is 2 or 3, q is 1, 2, 3 or 4, R⁴ is S or SO₂, and R⁵ is lower alkyl, lower alkoxy or halogen;

R is halogen or —COOR' wherein R' is lower alkyl; and Z is

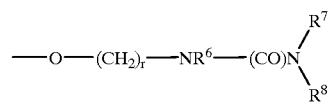

in which r is 0 or 1, R⁶ is H or OH, R⁷ is H or OH, and R⁸ is lower alkyl.

More preferably, Q is O, Ar¹ is

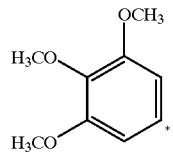

and

Ar³ is

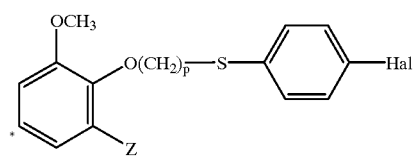

in which the * represent the points of binding and Hal is Cl or F. In this latter case, the compound synthesized has the structural formula

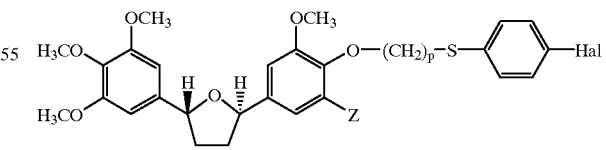

Specific compounds encompassed by this structural formula, which are preferred compounds to be synthesized using the present methodology, include ( ) trans-2-[5-(N'-methyl-N'-hydroxyureidyl-methyl)-3-methoxy-4-p-chlorophenylthioethoxyphenyl]-5-(3,4,5-trimethoxyphenyl) tetrahydrofuran, i.e., CMI-392

CMI-392

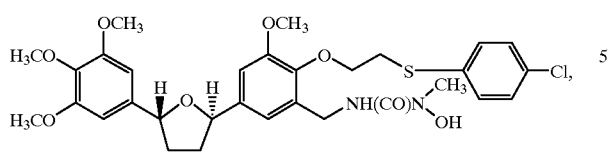

as well as variants thereof, particularly (±) trans-2-[5-(N'-methyl-N'-hydroxyureidylmethyl)-3-methoxy-4-p-chlorophenylthiopropoxyphenyl]-5-(3,4,5-trimethoxyphenyl)tetrahydrofuran, (±) trans-2-[5-(N'-methyl-N'-hydroxyureidylmethyl)-3-methoxy-4-p-fluorophenylthioethoxyphenyl]-5-(3,4,5-trimethoxyphenyl)tetrahydrofuran, and (±) trans-2-[5-(N'-methyl-N'-hydroxyureidylmethyl)-3-methoxy-p-fluorophenylthiopropoxyphenyl]-5-(3,4,5-trimethoxyphenyl)tetrahydrofuran, shown structurally as follows:

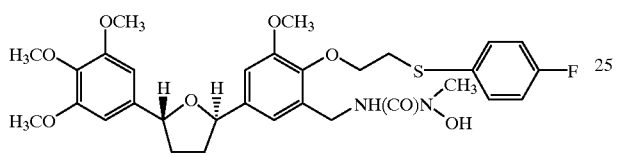

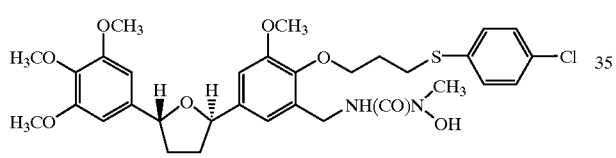

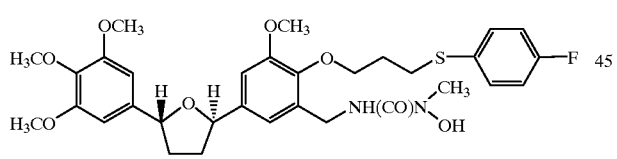

In another embodiment of the invention, processes are provided for preparing intermediates useful for synthesizing certain vinyl ketones or thioketones encompassed by structural formula (III). A key intermediate has the structural formula (VII)

(VII)

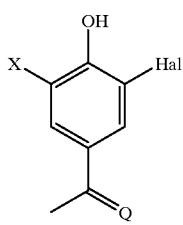

and is synthesized by treating the starting material (VIII)

(VIII)

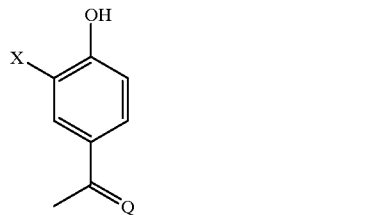

with a halogenating reagent $(Hal)_2$ in the presence of a carbonate salt, at room temperature, followed by acidification of the reaction mixture. The reaction is exemplified in part (a) of the Example herein, using acetovanillone as a starting material and iodine as the halogenating reagent, thus providing 5-iodoacetovanillone as the product. In the above formulae, Hal is a halogen atom, Q is S or O, X is selected from the group consisting of alkyl, alkenyl, alkynyl, halogen, halogenated alkyl, halogenated alkenyl, halogenated alkynyl, $-OR^1$, $-(CH_2)_nOR^1$, $-O(CH_2)_nOR^1$, $-SR^1$, $-(CH_2)_nSR^1$, $-S(CH_2)_nSR^1$, $-COOR^1$, $-(CO)R^1$, $-NR^2R^3$, $-(CO)NR^2R^3$, $-O(CO)NR^2R^3$, and $-CN$, wherein $R^1$, $R^2$ and $R^3$ are independently hydrogen, alkyl or aryl, m is 1, 2 or 3, and n is an integer in the range of 1 to 6. Preferably, Hal is I, Q is O, and X is methoxy.

Another important reaction for preparing an intermediate useful for synthesizing certain of the vinyl ketones and diketones encompassed by structural formula (m) involves preparation of a compound having the structural formula (IX)

(IX)

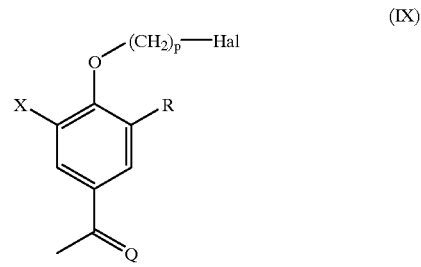

by treating the starting material (X)

(X)

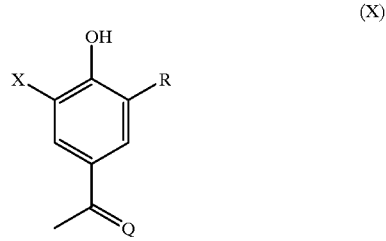

with a dihaloalkane $Hal-(CH_2)_p-Hal$ at elevated temperature for a time sufficient to ensure complete reaction, wherein R is halogen or a lower alkyl ester $-COOR'$ where R' is lower alkyl, the Hal are independently halogen, p is 2 or 3, Q is O or S, and X is selected from the group consisting of alkyl, alkenyl, alkynyl, halogen, halogenated alkyl, halogenated alkenyl, halogenated alkynyl, $-OR^1$, $-(CH_2)_nOR^1$, —O(CH$_2$)$_n$OR$^1$, —SR$^1$, —(CH$_2$)$_n$SR$^1$, —S(CH$_2$)$_n$SR$^1$, —COOR$^1$, —(CO)R$^1$, —NR$^2$R$^3$, —(CO)NR$^2$R$^3$, —O(CO)NR$^2$R$^3$, and —CN, wherein R$^1$, R$^2$ and R$^3$ are independently hydrogen, alkyl or aryl, m is 1, 2 or 3, and n is an integer in the range of 1 to 6. Preferably, R is iodo or —COOCH$_3$, Q is O, and X is methoxy. The reaction is exemplified in part (c) of Example 1 below, wherein 5-iodoacetovanillone is converted to 4-[2-bromoethoxy]-3-iodo-5-methoxy acetophenone.

In a further embodiment of the invention, a process is provided for preparing the vinyl ketone or thioketone (III)

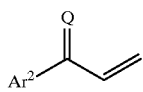
(III)

in which Q is O or S and Ar$^2$ is as defined above, i.e., Ar$^2$ is selected from the group consisting of aryl, aralkyl, heteroaryl and heteroaralkyl, optionally substituted with 1 to 3 substituents. The first step of the process involves treating the ketone or thioketone (XI)

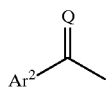
(XI)

with paraformaldehyde and a halide salt of a di(lower alkyl)amine (R$^9$)$_2$NH$_2^+$Hal$^-$, in which R$^9$ is lower alkyl and Hal is a halogen atom, followed by treatment with an acid, to provide the Mannich salt (XII)

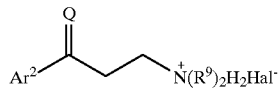
(XII)

The reaction conditions employed are those typically used in connection with carrying out the Mannich reaction; see, e.g., Scott et al. (1972) J. Am. Chem. Soc. 94:4779, Danishefsky et al. (1977) J. Am. Chem. Soc. 99:6066, and Wender et al. (1980) J. Am. Chem. Soc. 10:6340. Generally, the reaction is run in water, ethanol, isopropanol or acetic acid. The formaldehyde is introduced as is or in an aqueous solution. The amine, as noted above, is introduced as a halide salt, preferably as a hydrochloride salt. Reaction is preferably conducted at reflux for at least about 20 minutes. Preparation of a Mannich salt is exemplified in part (d) of Example 1.

The Mannich salt (XII) is then quaternized, followed by elimination, as follows. The salt (XII) is dissolved in a basic solution, typically a sodium hydroxide solution, and extracted into an organic layer such as ethyl acetate or the like. The extracted product is then treated with an alkyl halide e.g. a dialkyl or trialkyl halide, e.g., methyl iodide, and allowed to react for on the order of 5–6 hours. The quaternary ammonium salt (XII)

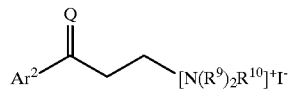
(XIII)

in which R$^1$ is hydrogen or alkyl, preferably lower alkyl, may be obtained by filtration and is then preferably air-dried prior to conducting the elimination reaction. Elimination is effected by heating an aqueous solution of the quaternary ammonium salt, adding a suitable solvent such as ethyl acetate, and extracting the desired product, i.e., the vinyl ketone or thioketone (III). Parts (e) and (f) of Example 1 below exemplify quaternization of a Mannich salt followed by elimination.

Preferably, Ar$^2$ in the foregoing reaction has the structure

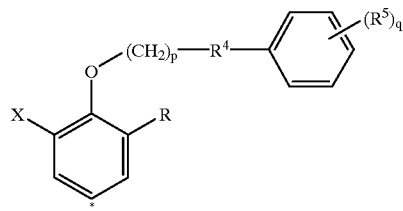

in which * represents the point of binding, p is 2 or 3, R$^4$ is S or SO$_2$, R$^5$ is lower alkyl, lower alkoxy or halogen, q is 1, 2, 3 or 4, R is halogen or a lower alkyl ester —COOR' where R' is lower alkyl, and X is selected from the group consisting of alkyl, alkenyl, alkynyl, halogen, halogenated alkyl, halogenated alkenyl, halogenated alkynyl, —OR$^1$, —(CH$_2$)$_n$OR$^1$, —O(CH$_2$)$_n$OR$^1$, —SR$^1$, —(CH$_2$)$_n$SR$^1$, —S(CH$_2$)$_n$SR$^1$, —COOR$^1$, —(CO)R$^1$, —NR$^2$R$^3$, —(CO)NR$^2$R$^3$, —O(CO)NR$^2$R$^3$, and —CN, wherein R$^1$, R$^2$ and R$^3$ are independently hydrogen, alkyl or aryl, m is 1, 2 or 3, and n is an integer in the range of 1 to 6. More preferably, R is iodo or —COOCH$_3$, R$^4$ is S, R$^5$ is chloro or fluoro, and x is lower alkoxy.

In other embodiments of the invention, novel compounds are provided that may be isolated and identified in the foregoing syntheses, and that useful as starting materials and/or intermediates in the preparation of diaryl-substituted heterocycles. One of these compounds is compound (XIV), as follows:

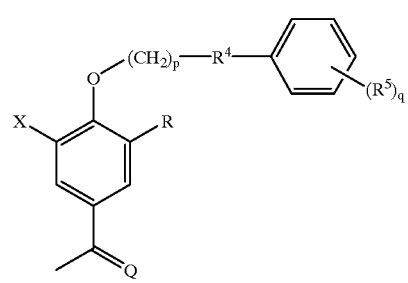
(XIV)

In compound (XIV):

X is selected from the group consisting of alkyl, alkenyl, alkynyl, halogen, halogenated alkyl, halogenated alkenyl, halogenated alkynyl, —OR$^1$, —(CH$_2$)$_n$OR$^1$, —O(CH$_2$)$_n$OR$^1$, —SR$^1$, —(CH$_2$)$_n$SR$^1$, —S(CH$_2$)$_n$SR$^1$, —COOR$^1$, —(CO)R$^1$, —NR$^2$R$^3$, —(CO)NR$^2$R$^3$, —O(CO)NR$^2$R$^3$, and —CN, wherein R$^1$, R$^2$ and R$^3$ are independently hydrogen, alkyl or aryl, m is 1, 2 or 3, and n is an integer in the range of 1 to 6;

Q is O or S;

R$^4$ is S or SO$_2$;

R$^5$ is lower alkyl, lower alkoxy or halogen;

p is 2 or 3;

q is 1, 2, 3 or 4; and

R is halogen or a lower alkyl ester —COOR' where R' is lower alkyl.

Preferably: X is lower alkoxy; Q is O; R$^4$ is S; R$_5$ is halogen; q is 1; and R is iodo or —COOCH$_3$. Most preferably, X is methoxy; and R$^5$ is Cl or F, and is in the para position.

Another novel compound useful as a starting material and/or intermediate in the synthesis of diaryl-substituted heterocycles, as described and claimed herein, has the structure of formula (XV):

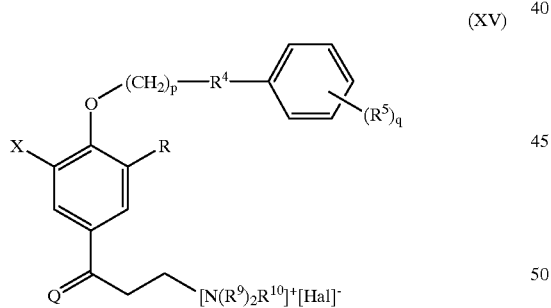

(XV)

In compound (XV):

X is selected from the group consisting of alkyl, alkenyl, alkynyl, halogen, halogenated alkyl, halogenated alkenyl, halogenated alkynyl, —OR$^1$, —(CH$_2$)$_n$OR$^1$, —O(CH$_2$)$_n$OR$^1$, —SR$^1$, —(CH$_2$)$_n$SR$^1$, —S(CH$_2$)$_n$SR$^1$, —COOR$^1$, —(CO)R$^1$, —NR$^2$R$^3$, —(CO)NR$^2$R$^3$, —O(CO)NR$^2$R$^3$, and —CN, wherein R$^1$, R$^2$ and R$^3$ are independently hydrogen, alkyl or aryl, m is 1, 2 or 3, and n is an integer in the range of 1 to 6;

Q is O or S;

R$^4$ is S or SO$_2$;

R$^5$ is lower allyl, lower alkoxy or halogen;

p is 2 or 3;

q is 1, 2, 3 or 4;

R is halogen or a lower alkyl ester —COOR' where R' is lower alkyl;

Hal is a halogen atom;

R$^9$ is lower alkyl; and

R$^{10}$ is hydrogen or lower alkyl.

Preferably: X is lower alkoxy; Q is O; R$^4$ is S; R$^5$ is halogen; q is 1; R is iodo or —COOCH$_3$; and Hal is iodo. More preferably, X is methoxy, R$^5$ is Cl or F, and is in the para position, R$^9$ is methyl or ethyl, and R$^{10}$ is hydrogen or R$^9$.

Another novel compound useful as a starting material and/or intermediate in the presently disclosed and claimed syntheses has the structural formula (XVI)

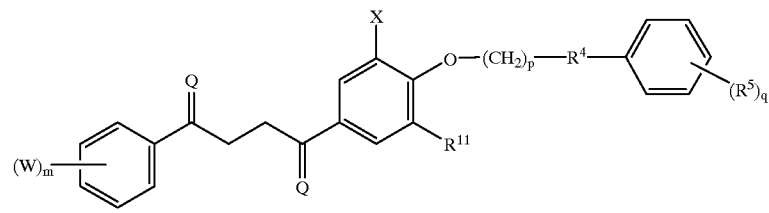

(XVI)

In compound (XVI):

the W are independently selected from the group consisting of alkyl, alkenyl, alkynyl, halogen, halogenated alkyl, halogenated alkenyl, halogenated alkynyl, —OR$^1$, —(CH$_2$)$_n$OR$^1$, —O(CH$_2$)$_n$OR$^1$, —SR$^1$, —(CH$_2$)$_n$SR$^1$, —S(CH$_2$)$_n$SR$^1$, —COOR$^1$, —(CO)R$^1$, —NR$^2$R$^3$, —(CO)NR$^2$R$^3$, —O(CO)NR$^2$R$^3$, and —CN, wherein R$^1$, R$^2$ and R$^3$ are independently hydrogen, alkyl or aryl, m is 1, 2 or 3, and n is an integer in the range of 1 to 6;

X is defined as for W;

m is 1, 2 or 3;

Q is O or S;

R$^4$ is S or SO$_2$;

R$^5$ is lower alkyl, lower alkoxy or halogen;

p is 2 or 3;

q is 1, 2, 3 or 4; and

R$^{11}$ is a halogen atom, a lower alkyl ester —COOR' where R' is lower alkyl, or —CN.

Preferably: W and X are independently lower alkoxy; m is 3; Q is O; R$^4$ is S; R$^5$ is halogen; R$^{11}$ is iodo, —COOCH$_3$ or —CN; q is 1; and Hal is iodo. More preferably, W and X are methoxy, and R$^5$ is Cl or F, and is in the para position.

Another novel compound useful as a starting material and/or intermediate in the present syntheses has the structural formula (XVII)

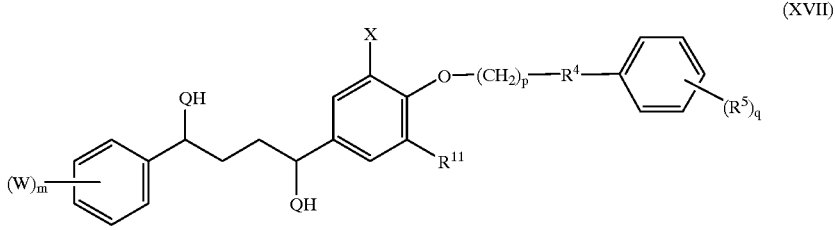

(XVII)

wherein:

the W are independently selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl, m is 1, 2 or 3, and n is an integer in the range of 1 to 6;

X is defined as for W;

m is 1, 2 or 3;

Q is O or S;

$R^4$ is S or $SO_2$;

$R^5$ is lower alkyl, lower alkoxy or halogen;

p is 2 or 3;

q is 1, 2, 3 or 4; and $R^{11}$ is a halogen atom, a lower alkyl ester —COOR' where R' is lower alkyl, or —CN.

Preferably: W and X are independently lower alkoxy; m is 3; Q is O; $R^4$ is S; $R^5$ is halogen; q is 1; and $R^{11}$ is iodo, —$COOCH_3$ or —CN. More preferably, W and X are methoxy, and $R^5$ is Cl or F, and is in the para position.

An additional novel compound has the structural formula (XVIII)

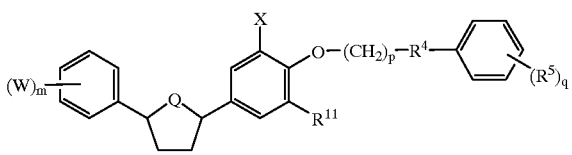

(XVIII)

wherein:

the W are independently selected from the group consisting of alkyl, alkenyl, alkynyl, halogen, halogenated alkyl, halogenated alkenyl, halogenated alkynyl, —$OR^1$, —$(CH_2)_nOR^1$, —$O(CH_2)_nOR^1$, —$SR^1$, —$(CH_2)_nSR^1$, —$S(CH_2)_nSR^1$, —$COOR^1$, —$(CO)R^1$, —$NR^2R^3$, —$(CO)NR^2R^3$, —$O(CO)NR^2R^3$, and —CN, wherein $R^1$, $R^2$ and $R^3$ are independently hydrogen, alkyl or aryl, m is 1, 2 or 3, and n is an integer in the range of 1 to 6;

X is defined as for W;

m is 1, 2 or 3;

Q is O or S;

$R^4$ is S or $SO_2$;

$R^5$ is lower alkyl, lower alkoxy or halogen;

p is 2 or 3;

q is 1, 2, 3 or 4; and $R^{11}$ is a halogen atom, a lower alkyl ester —COOR' where R' is lower alkyl, or —CN.

Preferably: W and X are independently lower alkoxy; m is 3; Q is O; $R^4$ is S; $R^5$ is halogen; q is 1; and R is iodo, —$COOCH_3$ or —CN. More preferably, W and X are methoxy, $R^5$ is Cl or F, and is in the para position, and $R^{11}$ is iodo, —$COOCH_3$ or —CN.

Following synthesis of the diaryl-substituted heterocycle (I) or (Ia), the compound may be converted to a pharmaceutically acceptable salt, ester, amide, prodrug, or other derivative or analog, or it may be modified by appending one or more appropriate functionalities to enhance selected biological properties. Such modifications are known in the art and include those which increase the rate of penetration into the skin or mucosal tissue, increase bioavailability, increase solubility, and the like. Conversion to salts, esters, amides, and the like may be carried out using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992).

As discussed above, the invention also includes methods useful for preparing diaryl-substituted heterocycles such as 2,5-diaryl-substituted tetrahydrofurans, particularly optically active substituted tetrahydrofurans.

These methods in general include functionalization of an alicyclic ring keto group, particularly a lactone, especially a γ-lactone such as γ-butyrolactone. The lactone is preferably substituted with an aromatic moiety, e.g. a phenyl group such as 3-benzyloxy-4-propoxy-5-propylsulfonylphenyl or 3-benzyloxy-4-propoxy-5-methylsulfonylphenyl. Such a lactone can be formed by a variety of procedures, e.g. by cyclization of a non-cyclic ester having a C3 moiety that is substituted by hydroxyl and a substituted aryl. The aryl group can have a desired substitution pattern, or be further modified at selected ring positions after lactone formation.

Such a lactone then can be reduced to provide a hydroxy-substituted alicyclic compound, particularly a hydroxy tetrahydrofuran. That compound is further functionalized by activating the hydroxyl alicyclic ring substituent followed by substitution of that ring position with an aryl reagent, e.g. a substituted phenyl magnesium bromide such as (3,4,5-trimethoxy phenyl)magnesium bromide. The di-aryl substituted alicyclic compound then can be further modified as desired, e.g. the aryl groups can be functionalized with various ring substituents.

These methods are preferably employed to provide an enantiomeric excess of one stereoisomer of a compound relative to other possible stereoisomer(s) of the compound, e.g. at least greater than about 60 or 70 mole percent of one stereoisomer of the compound than other(s), more preferably at least about 75, 80 or 85 mole percent of one stereoisomer of the compound than other(s), still more preferably at least about 90 or 95 mole percent of one stereoisomer of the compound than other(s).

These methods are particularly useful to prepare compounds of the following formula:

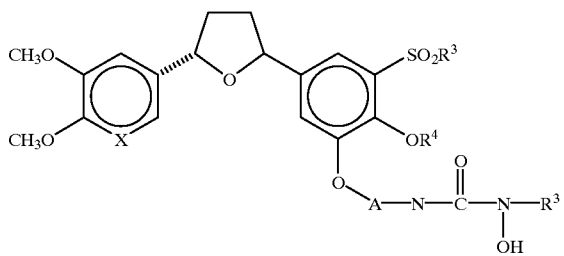

wherein in that formula:

A is optionally substituted lower alkyl, lower alkyl-alkoxy, lower alkenyl, lower alkynyl, alkaryl or aralkyl;

$R^3$ and $R^4$ are each independently optionally substituted alkyl, alkenyl, alkynyl, aryl, aralkyl, alkaryl, hydrogen, $C_{1-6}$alkoxy-$C_{1-10}$ alkyl, $C_{1-6}$ alkylthio-$C_{1-10}$ alkyl;

X is N or $C(OCH_3)$; and pharmaceutically acceptable salts thereof.

These methods are further exemplified in the following Scheme 1, which depicts the synthesis of optically active CMI-546. See also Example 2 which follows. The same synthesis can be employed for preparation of CMI-568, including optically active stereoisomers of CMI-568, by formation of a methylsufonylphenyl group rather than a propylsulfonylphenyl group.

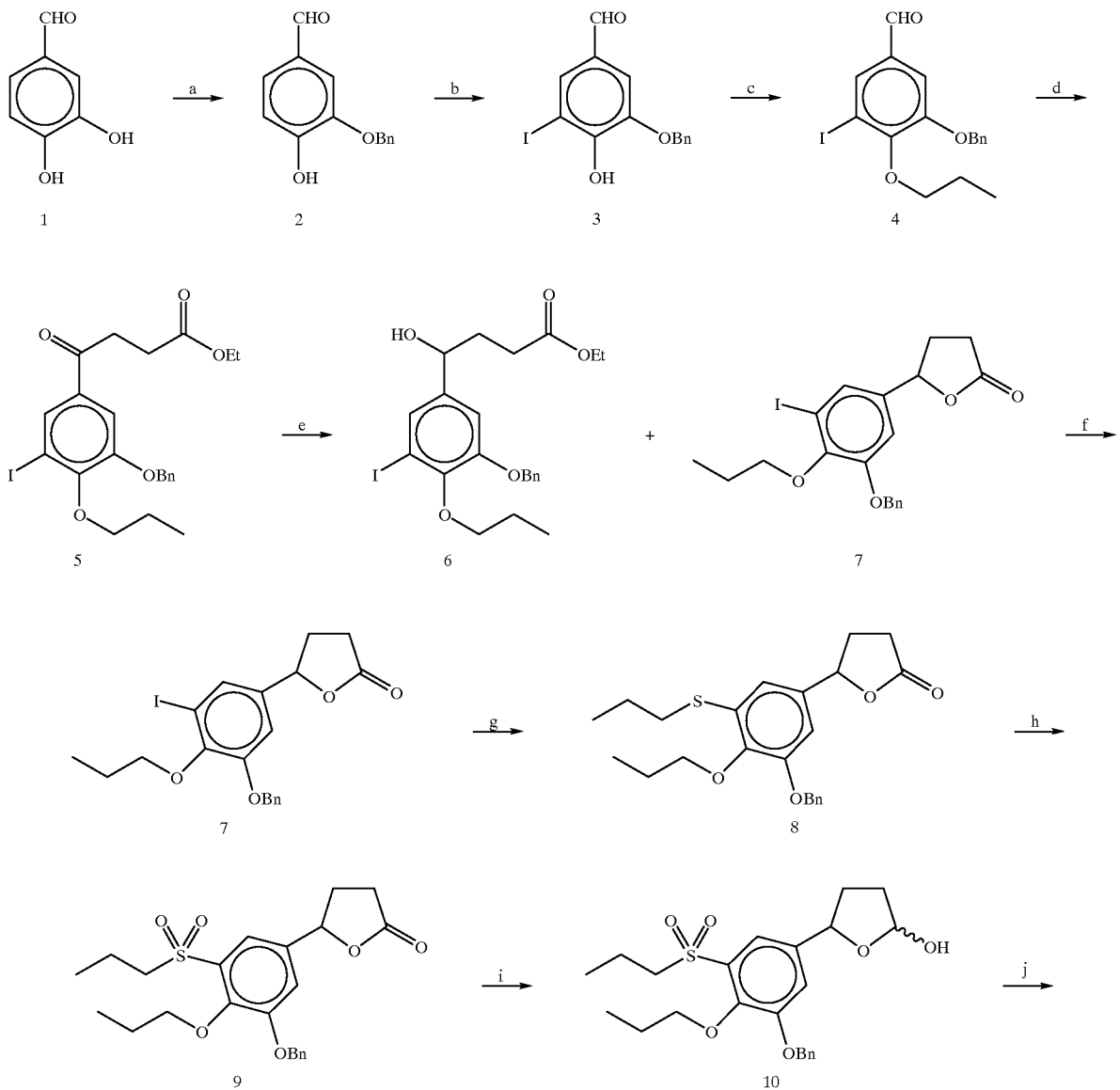

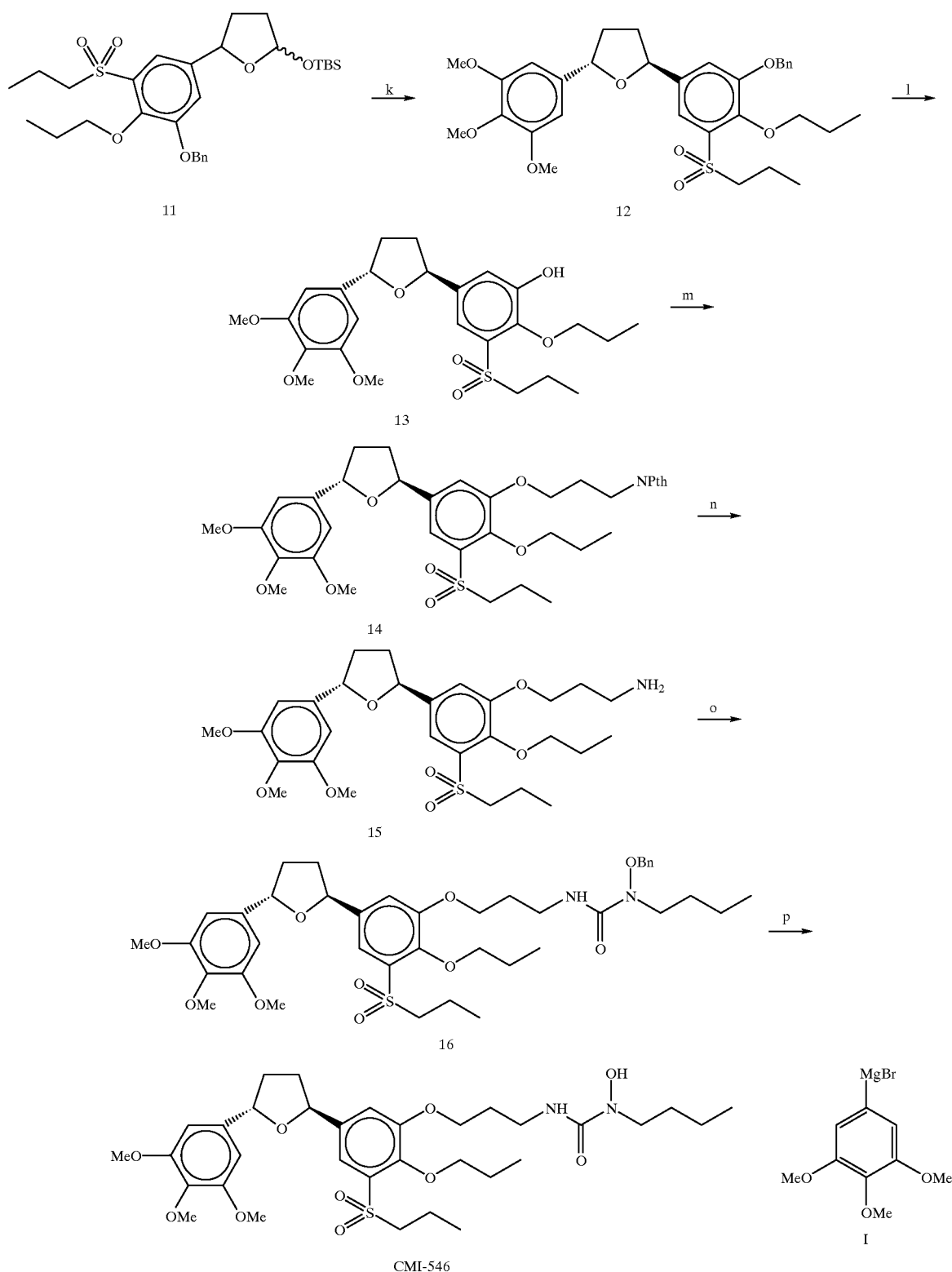
Reagents: (a) Ethanolic 2N KOH, Bn-Cl (Bn=benzyl) RT, 12 h, 29%; (b) I$_2$, 3.2% NaOH, 85–90° C., 8 h, 79%; (c) 1-Bromopropane, K$_2$CO$_3$, DMF, 75–80° C., 12 h, 82%; (d) i) NaCN, DMF, RT, 45 min ii) Ethyl acrylate, DMF, RT, 45 min., 74%; (e) NaBH$_4$, EtOH, 0° C., 10 min; (f) PTSA, DCM, 12 h, 79% (two steps); (g) Propyl disulphide, Copper powder, DMF, 100° C., 24 h, 86%; (h) m-CPBA, DCM, 0° C.-RT, 2 h, 73%; (i) DIBAL-H, Toluene, −78° C., 1 h, 99%; (j) TBDMS-Cl, Imidazole, DMF, RT, 3.5 h, 97%; (k) i)TMS-Br, DCM, −78° C., 90 min ii) I, Li$_2$CuCl$_4$, THF, −78° C., 71%; (l) Pd/C H$_2$, EtOAc, RT, balloon pressure, 2 h, 61%; (m) K$_2$CO$_3$, Acetone, Br(CH$_2$)$_3$Npth reflux, 16 h, 94%; n) NH$_2$NH$_2$.H$_2$O, EtOH, reflux, 10 h; o) i) Triphosgene, Et$_3$N, DCM, reflux, 2 h, ii) CH$_3$(CH$_2$)$_3$NHOBn, Et$_3$N, 3 h, RT, 80%; p) Pd/C, H$_2$, EtOAc, RT, 6 h, balloon pressure, 75%.

In another aspect, additional methods are provided useful for preparing heterocycles having di-carbocyclic aryl or heteroaromatic substitution (i.e. di-aryl herein), particularly aryl-substituted tetrahydrofurans, such as 2,5-diaryl-substituted tetrahydrofurans.

These methods in general include a coupling-type reaction of a compound that has an acetylene moiety, preferably a primary acetylene, substituted at a benzylic carbon, or other carbon having an aryl moiety (e.g. naphthyl or other carbocyclic aryl, or heteroaryl). The benzylic carbon also preferably has hydroxy or keto substitution. The acetylene reagent can be readily provided by reaction of an aromatic aldehyde such as optionally substituted benzaldehyde with acetylenemagnesium bromide.

The acetylene compound is reacted with a Grignard reagent, e.g. ethylmagnesium bromide at a temperature and time sufficient for reaction, e.g. at above 50° C. such as 60° C. for at least 30 minutes, preferably 60 or 90 minutes. The acetylene group of that product then can be saturated, e.g. via hydrogenation, and then the di-hydroxy compound reacted such as in the presence of a suitable acid to provide a diaryl tetrahydrofuran.

The diaryl tetrahydrofuran compound formed in the method can be modified as desired, e.g. the aryl groups can be modified to provide various ring substituents as desired.

For example, in one approach, the diaryl tetrahydrofuran compound is suitably reacted to modify at least one of the diaryl groups by adding halogen and hydroxyl thereto. In particular, the compound can be reacted so that one of the diaryl groups is halogenated and hydroxylated. That compound can be further reacted with a suitable di-haloalkyl compound, e.g., di-bromoethane, to alkylate the hydroxyl group of the compound, thereby adding an alkoxy group. Preferred reaction conditions maintain halogen on the alkoxy group which halogen can be reacted with a suitably substituted mercaptobenzene compound such as p-chloro-mercaptobenzene. The resulting product can be used to synthesis compounds of this invention and particularly CMI-392.

A particular embodiment of these methods is exemplified in the following Scheme 2, which scheme depicts the synthesis of various intermediates of CMI-392. See also Example 3 which follows.

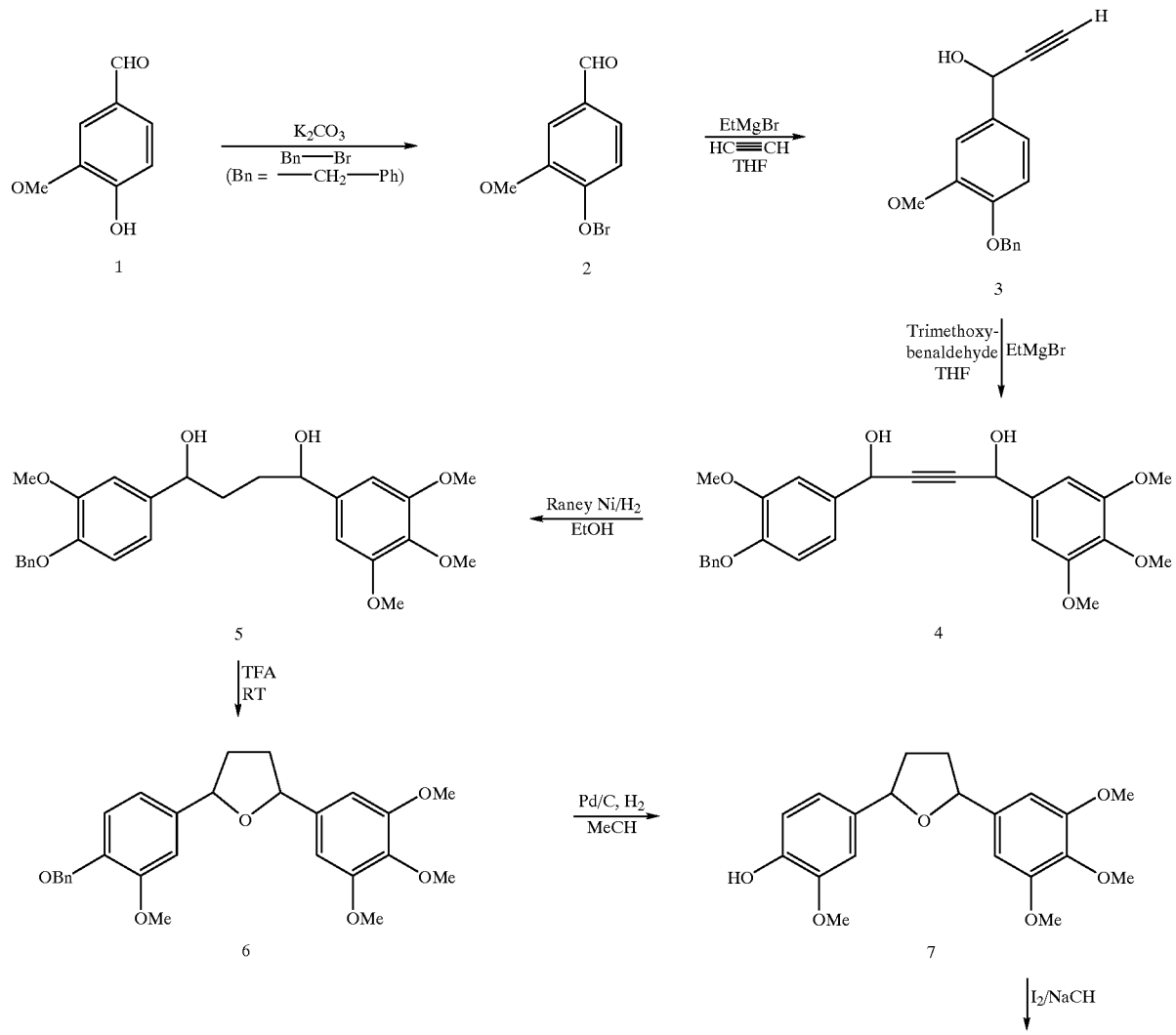

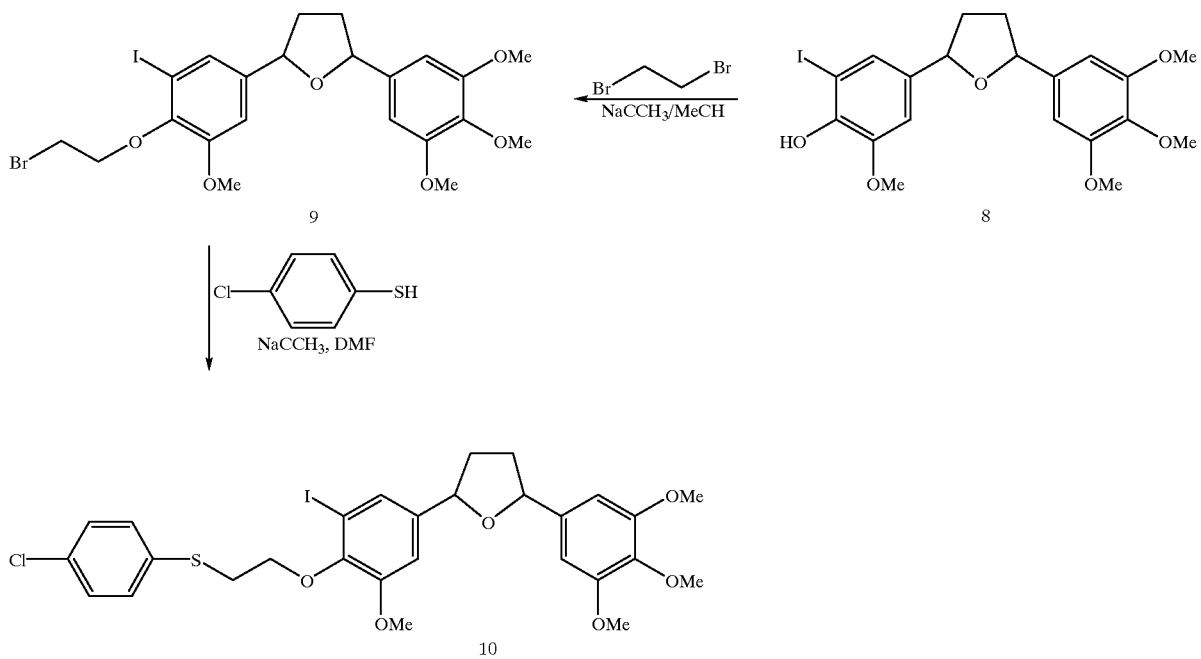

Figure 2A:
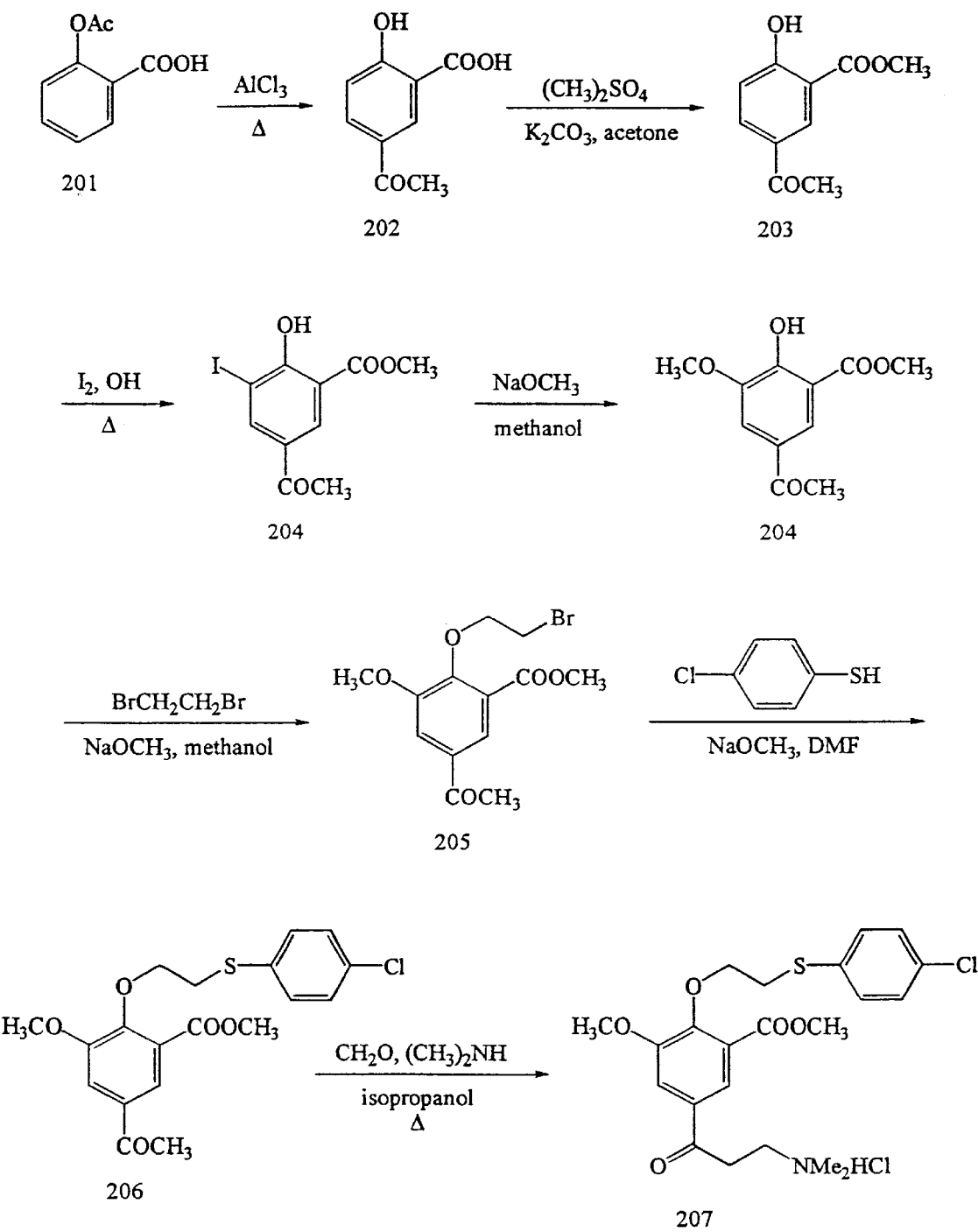
FIGS. 2a–2c schematically illustrate an alternative method for synthesizing crystalline CMI-392 using acetyl salicylic acid (aspirin) as a starting material.
Figure 2B:
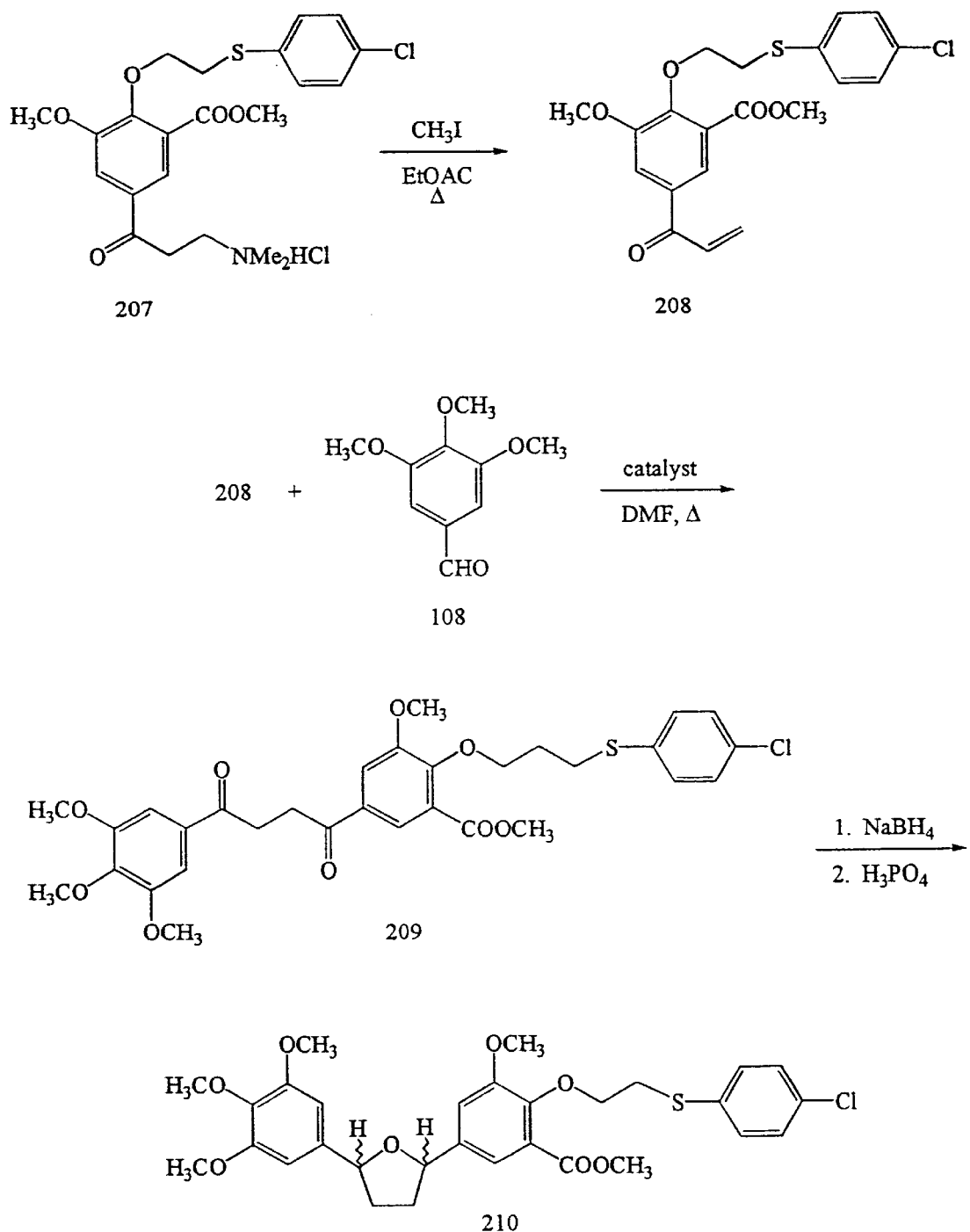
Figure 2C:
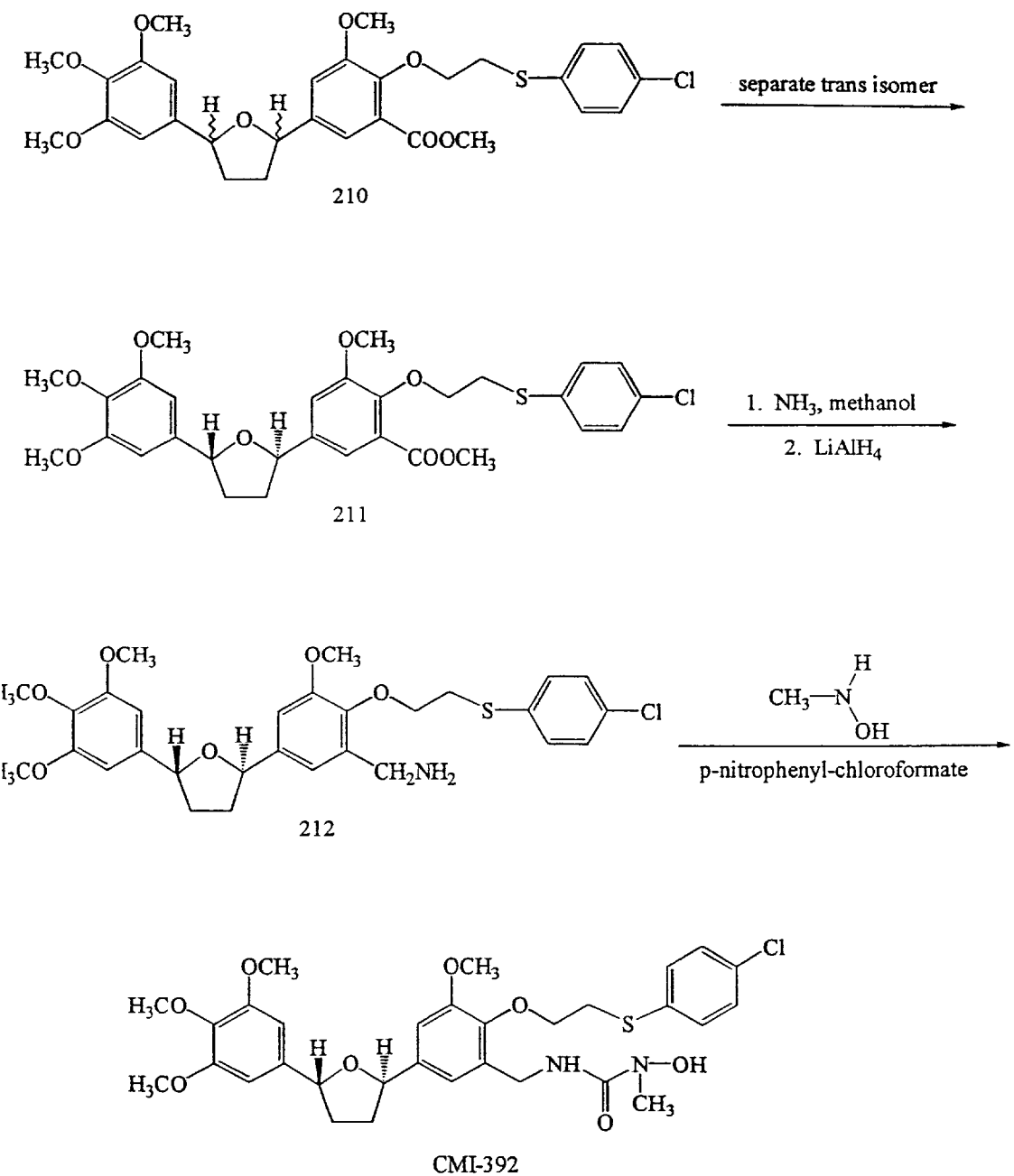

Further, as detailed in FIGS. 2a through 2c, compounds disclosed herein, including diar-yl-substituted tetrahydrofurans, particularly CMI-392, may be conveniently synthesized with a starting reagent of methyl salicylate (aspirin).

More particularly, as generally depicted in FIGS. 2a through 2C, methyl salicylate may be reacted with a Friedel-Crafts catalyst such as $AlCl_3$ typically with heating to provide a Fries rearrangement product, such as compound 202 in FIG. 2a. That compound 202 can be alkylated, particularly methylated, e.g. with dimethyl sulfate in the presence of anhydrous potassium carbonate to provide an alkyl ester, typically a $C_{1-6}$ alkyl ester-such as methyl ester 203, which then can be reacted with iodine under basic conditions to provide compound 204 shown in FIG. 2a. That iodide phenyl substituent can be substituted, e.g. with to provide a methoxy or other $C_{1-6}$ alkoxy ring substituent followed by O-alkylation e.g. by use of 1,2-dibromethane to provide compound 205 shown in FIG. 2a. Compound 205 then can be treated with base (preferably mild base such as $NaOCH_3$) followed by p-chlorothiophenol to furnish compound 206 of FIG. 2a, which then is reacted with paraformaldehyde and suitable amine salt such as dimethylamine HCl in an appropriate solvent such as an alcohol, particularly isopropanol, to yield Mannich salt 207 upon heating, as shown in FIGS. 2a and 2b.

That compound 207 then is converted to a quaternary ammonium salt with methyl iodide which on heating is converted to enone 208. Coupling of the enone 208 and trimethoxy benzaldehyde 108 in a suitable solvent such as DMF provides diketone compound 209, as shown in FIG. 2b. The diketone 209 then can be reduced with a suitable reducing agent such as $NaBH_4$ followed by cyclization in the presence of acid to provide substituted tetrahydrofuran 210. The separated trans isomer 211 is treated with ammonia in methanol or other alcohol and then reduced (e.g. $LiAlH_4$) to furnish the amine 212, as shown in FIG. 2c. Reaction of that compound 212 with p-nitrophenyl chloroformate and N-methylhydroxyamine in the presence of base such as triethyl amine provides CMI-392, which can be crystallized in a suitable solvent, preferably an alcohol, particularly isopropyl alcohol.

The agents prepared using the presently disclosed and/or claimed synthetic techniques are useful for treating humans and other animals suffering from inflammatory and/or immune disorders, and, in particular, disorders mediated by PAF or products of 5-lipoxygenase. For example, the compositions find utility in the treatment in inflammatory skin disorders, including, but not limited to, psoriasis, contact dermatitis, atopic dermatitis (also known as allergic eczema), exfoliative dermatitis, seborrheic dermatitis, erythemas (including erythema multiforme and erythema nodosum), discoid lupus erythematosus and dermatomyositis. The agents are particularly effective in treating psoriasis and atopic dermatitis. The formulations are administered topically, as ointments, creams, gels, patches, or the like, as described in the preceding section, within the context of a dosing regimen effective to bring about the desired result.

It is to be understood that while the invention has been described in conjunction with the preferred specific embodiments thereof, the foregoing description, as well as the example which follows, are intended to illustrate and not limit the scope of the invention. Other aspects, advantages and modifications will be apparent to those skilled in the art to which the invention pertains.

The following example is put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric. All solvents were purchased as HPLC grade and, where appropriate, solvents and reagents were analyzed for purity using common techniques. All reactions were routinely conducted under an inert atmosphere of argon, unless otherwise indicated.

All patents, patent applications, and publications cited herein are incorporated by reference in their entireties.

EXAMPLE 1

SYNTHESIS OF CMI-392

Figure 1B:
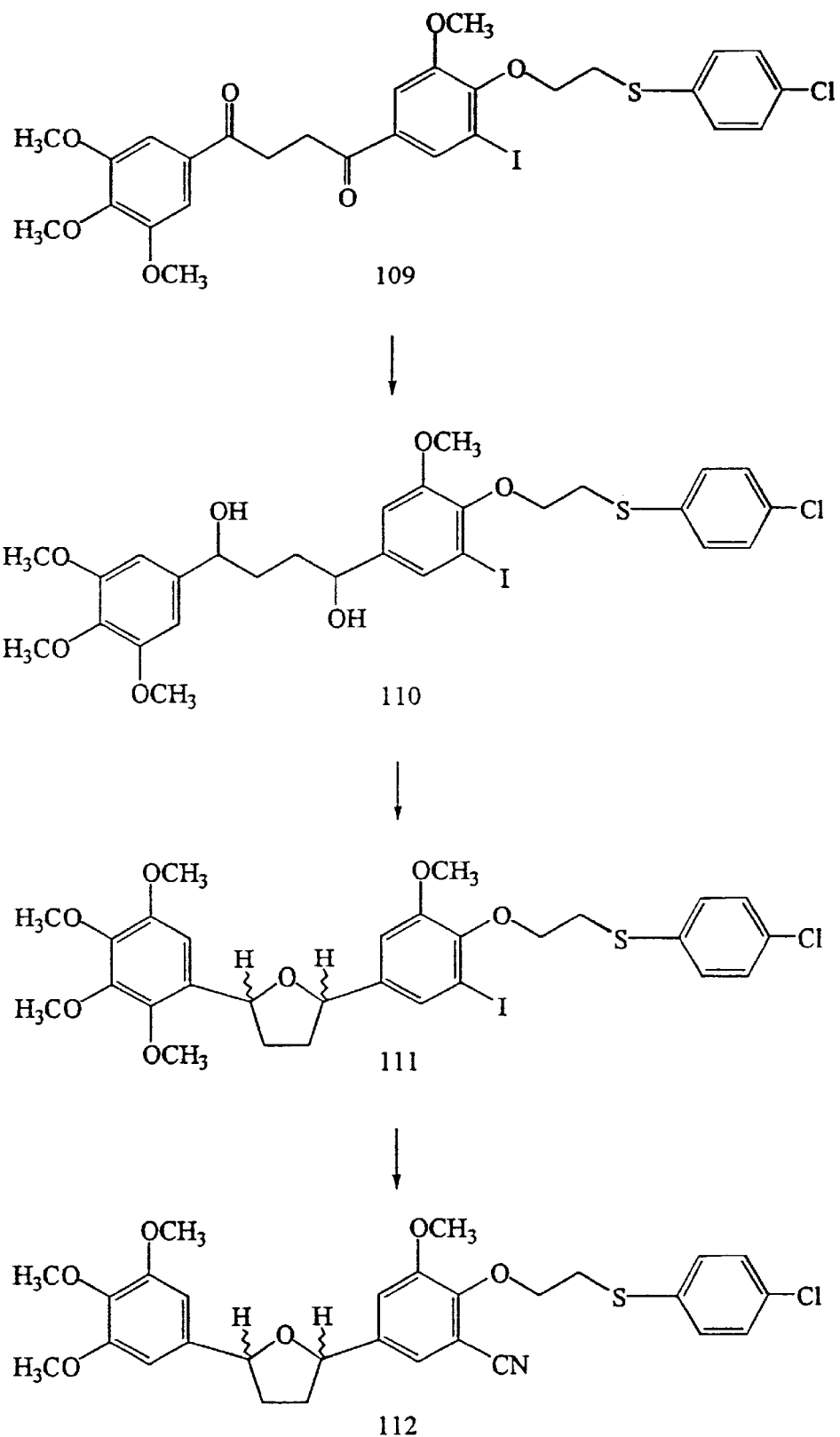
Figure 1C:
Figure 1C:
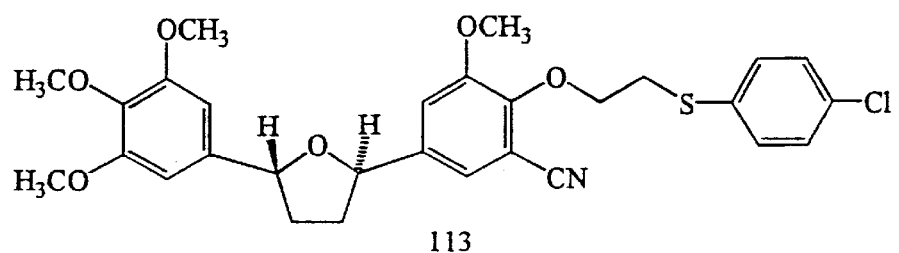
Figure 1C:
Figure 1C:
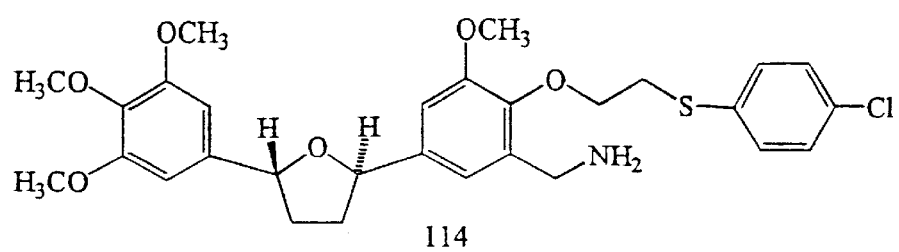
Figure 1C:
Figure 1C:
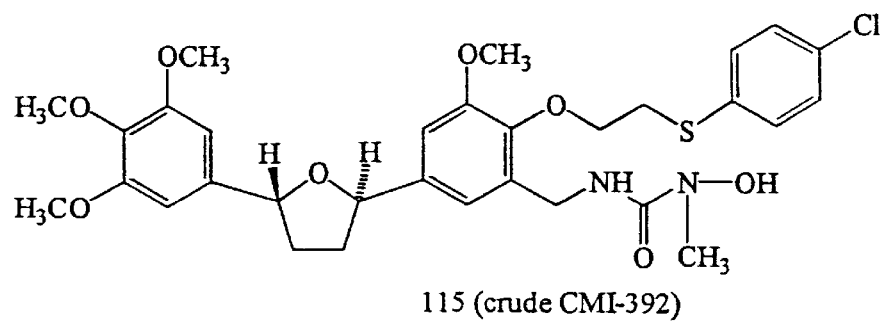
Figure 1C:

CMI-392, (±) trans-2-[5-(N'-methyl-N'-hydroxyureidylmethyl)-3-methoxy-4-p-chlorophenylthioethoxyphenyl]-5-(3,4,5-trimethoxyphenyl)-tetrahydrofuran, was prepared using the synthesis shown in FIGS. 1a through 1c, as follows:

(a) 5-Iodoacetovanillone (compound 102): Sodium hydrogen carbonate (657 g) was dissolved in water (8 L), acetovanillone (1.0 kg) was then added and the solution stirred for 0.5 hours. Iodine (1.828 kg) was added in 10–15 g portions over a period of 2 hours, and the reaction mixture was stirred for 18–20 hours at room temperature. The reaction was monitored by TLC (silica gel, solvent system: benzene). The reaction solution was acidified with concentrated HCl (175 ml) bringing the pH to about 2, and the solution stirred for an additional hour. The solid was collected by filtration, washed with 20% sodium dithionite solution (5 L) and water (5 L), and dried for 12–14 hours at room temperature. The crude product was crystallized from isopropyl alcohol (2 L). Yield: 1.51 kg (85%), purity: 91% (HPLC), m.p.: 175–176° C.

(b) 4-[2-Bromoethoxy]-3-iodo-5-methoxyacetophenone (compound 103): To a 10 L three neck round bottom flash containing 5-iodovanillone (compound 102, 1.0 kg) dissolved in DMF (5 L) containing potassium carbonate (1.417 kg), was added 1,2-dibromoethane (2.57 kg). The solution was heated to 60–70° C. for 4–5 hours. The reaction was monitored by TLC (silica gel, solvent system: 30% ethyl acetate in n-hexane). The solution was cooled to room temperature and the solid collected by filtration and washed with benzene (500 mL). The filtrate was concentrated under reduced pressure. The residue was dissolved in benzene (3 L), washed with water (2×1 L) and saturated brine solution (2×1 L). The organic layer was dried over sodium sulfate (500 g) and concentrated under reduced pressure to give compound. Yield: 1.025 kg (75%), purity: 87% (HPLC), m.p.: 82–83° C.

(c) 3-Iodo-5-methoxy-4-[2-p-chlorothiophenylethoxy]acetophenone (compound 104): A 10 L three neck round bottom flask fitted with a calcium chloride guard tube and containing TBF (2.5 L) was cooled to 0–5° C. and sodium methoxide (149 g) was slowly added over a 1 hour period. A solution of 0.362 kg p-chlorothiophenol in 1.0 L THF was then added over a 1-hr. period. The solution was stirred for another 1.5 hours at below 10° C., and then compound 103 (1.0 kg) in THF (1.5 L) was slowly added over a 1.5 hour period. The reaction was stirred at room temperature for 12–14 hours and monitored by TLC (silica gel, solvent system: 25% benzene in hexane). Saturated ammonium chloride (500 mL) was then added, the solution stirred for 1 hour, and the organic layer was separated and concentrated under reduced pressure. The residue was washed with water (2×2 L) and dried at room temperature for 24 hours. Yield: 1.08 kg (93%), purity: 90%, m.p.: 100–101° C.

(d) Mannich salt of 3-iodo-5-methoxy-4 [2-p-chlorothiophenylethoxy]acetophenone (compound 105): In a 5 L flask filter with a calcium chloride guard tube, compound 104 (500 g), paraformaldehyde (32 g), dimethylamine HCl (76 g) and concentrated HCl (20 mL) were combined and the contents refluxed for 2 hours. The reaction was monitored by TLC (silica gel, solvent system: 25% benzene in n-hexane). Paraformaldehyde (32 g) and dimethylamine HCl (76 g) were added to the reaction mixture twice, followed by reflux for 2 hours after each addition. The reaction was allowed to cool to room temperature, acetone (1.5 L) was added, and the reaction cooled to 0° C. for 4–5 hours. The solid was collected by filtration, washed with acetone (500 mL), and dried at room temperature for 2–3 hours. Yield: 325 g (54%), m.p.: 142–144° C.

(e) Quaternary ammonium salt of 3-iodo-5-methoxy-4-[2-p-chlorothiophenylethoxy]acetophenone (compound 306): Compound 305 (304 g) was dissolved in ethyl acetate (1.0 L) and then 3.5% solution of NaOH (1 L) was added. The reaction mixture was stirred for 0.5 hours, the organic layer was separated, and the aqueous layer extracted with ethyl acetate (2×250 mL). The organic layers were combined, washed with water (2×500 mL) and dried over sodium sulfate. The inorganic salts were separated by filtration. The organic filtrate was cooled to 0° C. in a 3 L round bottom flask and then methyl iodide (106 g) was added in three portions over 0.5 hours. The reaction mixture was then stirred at room temperature for 5–6 hours. The solid was collected by filtration and washed with ethyl acetate (500 mL). Yield: 310 g (81%), m.p.: 135–137° C.

(f) 3-Iodo-5-methoxy-4-(2-p-chlorothiophenylethoxy) phenyl vinyl ketone (compound 107): In a 5 L round bottom flask, compound 106 (300 g) was added to water (1.5 L) that was warmed to 35–40° C. Then, ethyl acetate (1.0 L) was added and the reaction solution refluxed for 1 hour. Upon cooling to room temperature, the organic layer was separated, and the aqueous layer was again refluxed with ethyl acetate (2×250 mL). The combined organic layers were dried over sodium sulfate and concentrated under reduced pressure. Yield: 186 g (86%), purity: 95% (HPLC), m.p.: 91–92° C.

(g) 1-(3',4',5'-Trimethoxyphenyl)-4-[3"-iodo-5"-methoxy-4"-(2-p-chlorothiophenyl-ethoxy)phenyl]-1,4-dioxobutane (compound 109): 3-Benzyl-5-(2-hydroxyethyl)-4-methyl-thiazolium chloride catalyst (45.5 g) and 3,4,5-trimethoxybenzaldehyde (compound 108, 165 g) were dissolved with stirring in DMF (1 L) in a 5 L round bottom flask containing a calcium chloride guard, and then compound (307) (400 g) was added. After about 0.5 hours of stirring, triethylamine (128 g) was slowly added and the reaction mixture heated to 70–80° C. until completion as determined by TLC (silica gel, solvent system: 40% ethyl acetate in n-hexane). The reaction mixture was then cooled to room temperature and 10% HCl (4 L) was added slowly with vigorous stirring for about 1 hour. The aqueous layer was decanted, and the product washed with water (2×2 L) with decantation. The crude product was stirred in isopropyl alcohol (1 L) for 1 hour, the solid collected by filtration and washed with isopropyl alcohol (500 mL). Yield: 425 g (75.2%), m.p.: 105–107° C.

(h) 1-[3'-Iodo-5'-methoxy-4'-(2-p-chlorothiophenylethoxy)phenyl-4-(3",4",5"-trimethoxyphenyl)-butan-1,4-diol (compound 110): Compound 109 (400 g) was dissolved in THF (2 L) and methanol (100 mL), and the 5 L round bottom flask was cooled to 0° C. NaBH$_4$ (25 g) was then added in 2–3 g portions over a period of 1 hour. Stirring was continued for 2 hours at below 10° C. The reaction was then quenched with a saturated solution of ammonium chloride (100 mL) and stirred for another hour. The solvents were removed under reduced pressure, benzene (1.5 L) and water (1.0 L) were added to the residue, the organic layer was separated, and the aqueous layer was extracted once again with benzene (0.5 L). The combined organic layers were washed with water (0.5 L)

and then with brine (2×0.5 L), dried over sodium sulfate and filtered. The compound in the filtrate was used in the next step without further purification.

(i) Cis/trans-2-(3',4',5'-Trimethoxyphenyl)-5-[3"-iodo-5"-methoxy-4-(2-p-chlorothiophenylethoxy)phenyl] tetrahydrofuran (compound 111). The benzene solution containing compound 110 (2 L), prepared in the preceding step, and orthophosphoric acid (130 mL) were placed in a 3 L round bottom flask and refluxed for 2 hours. The contents were cooled to room temperature and the upper benzene layer was decanted. The benzene layer was washed with water (500 mL), 20% sodium bicarbonate (2×500 mL) and finally with brine (2×500 mL). The organic layer was dried over sodium sulfate and concentrated under reduced pressure to give an oily compound. Yield: 370 g (94%).

(j) Cis/trans-2-(3',4',5'-Trimethoxyphenyl)-5-[3'-cyano-5"-methoxy-4"-(2-p-chlorothiophenylethoxy) phenyltetrahydrofuran (compound 112). In a 3 L round bottom flask, compound (111) (370 g) was dissolved in DMF (900 mL), cuprous cyanide (75.7 g) was then added in one portion, and the reaction mixture was heated to 120–125° C. for 45 hours. The reaction was monitored by TLC (silica gel, solvent system: 30% ethyl acetate in n-hexane). The mixture was cooled to room temperature, water (4 L) and benzene (1 L) were added, and the solid was filtered and washed with benzene (500 mL). The organic layer was separated and washed with water (500 mL), brine (2×500 mL), dried over sodium sulfate, and filtered through a silica gel bed. Benzene solution was concentrated under reduced pressure, and the residue used in the next step without further purification. Yield: 230 g (73.4%).

(k) Crystallization of the cis-trans mixture of compound 112 to give pure trans compound 113: The cis-trans mixture of compound 112 (230 g) was dissolved in ethyl acetate (1 L) and n-hexane (900 mL) was slowly added with stirring until turbidity of the solution persisted. The solution was cooled to room temperature, then seeded with pure trans compound, and left standing at −10° C. for 10–12 hours. The white solid was filtered and washed with 20% ethyl acetate in n-hexane four times. The white product was washed with n-hexane (100 mL) and dried under vacuum for 2 hours.

The organic layers were combined and concentrated under reduced pressure. The residue (150 g) was dissolved in chloroform (270 mL) and trifluoroacetic acid (30 mL) was added. The mixture was stirred for 7–8 hours at room temperature. Water (200 mL) was added and the organic layer separated, washed with water (200 mL), 20% sodium bicarbonate solution (200 mL) and finally with brine (200 mL), and dried over sodium sulfate. Chloroform was removed under reduced pressure. The residue was dissolved in ethyl acetate (220 mL) and hexane (500 mL) was added with stirring until turbidity persisted. As above, the solution was seeded with pure trans compound, and left standing at −10° C. for 12–14 hours. The solid was collected by filtration, washed four times with 20% ethyl acetate in n-hexane, and dried under vacuum for 2 hours. The solid thus obtained was thoroughly mixed with the first solid, the mixture suspended in hexane (150 mL), filtered, and dried. Yield: 105 g (45.6%), purity: 97% trans, 1.2% cis, m.p.: 85–86° C.

(l) Trans-2-(3'4',5'-Trimethoxyphenyl)-5-[3'-aminomethyl-5"-methoxy-4"-(2-p-chlorothiophenylethoxy) phenyl]tetrahydrofuran (compound 114). Compound 113 (100 g) was dissolved in THF (500 mL) and cooled to 0° C. in a 2 L round bottom flask. Then alane-N,N-dimethylethylamine complex in toluene (0.5 M, 800 mL) was slowly added under a $N_2$ atmosphere. The reaction mixture was then refluxed for 2 hours, stirred at room temperature for 1 hour, and then cooled to 0° C. The reaction was quenched with saturated sodium chloride solution (50 mL), the solid collected by filtration, and washed with hot TBF (2×100 mL). The combined filtrate and washings were concentrated under reduced pressure. To the residue obtained, toluene (100 mL) was added and then removed under reduced pressure to give a thick oil. Yield: 95.6 g (95%).

(m) CMI-392, (±)trans-2-[5-(N'-methyl-N'-hydroxyureidylmethyl)-3-methoxy-4-p-chloro-phenylthioethoxyphenyl]-5-(3,4,5-trimethoxyphenyl) tetrahydrofuran: To a 2 L round bottom flask containing toluene (400 mL) cooled to 0° C. was added p-nitrophenylchloroformate (36 g). Then, compound 114 (95 g) dissolved in toluene (400 mL) was slowly added followed by triethylamine (18 g). The reaction mixture was stirred at 0° C. for 2.5 hours. In a separate flask, to N-methylhydroxylamine HCl (21.3 g) in DCM (200 mL) was added triethylamine (27 g). The resultant mixture was added to the reaction vessel above along with triethylamine (18 g). The reaction mixture was heated at 60–65° C. for 3 hours, and monitored by TLC (silica gel, solvent system: 60% ethyl acetate in hexane). The reaction mixture was cooled to room temperature, water (500 mL) was then added, and the organic layer was separated and washed with 10% potassium hydrogen sulfate (1×300 mL, 2×150 mL), IN NaOH solution (800 mL), brine (4×250 mL), 10% potassium hydrogen sulfate solution (200 mL) and finally with brine (500 mL). The organic layer was dried over sodium sulfate and concentrated to give an oil. Yield: 105 g (98%).

(n) Purification of CMI-392: The oily product obtained in the preceding step was dissolved in isopropyl alcohol (300 mL) by warming to 45–50° C. The solution was then cooled to −10° C. for 12 hours. To the cold solution, n-hexane (300 mL) was added, seeded with pure CMI-392, and left below −10° C. for another 10–12 hours. The solid was collected by filtration, washed with 5% isopropyl alcohol in n-hexane (100 mL) and dried. The product was recrystallized from isopropyl alcohol in hexane (1:1) as above, and washed with 10% isopropyl alcohol in n-hexane (4×150 mL). The compound was then suspended in n-hexane (100 mL), filtered, and dried under vacuum for 2 hours. Yield: 70 g (67%), purity: 98% (BILC), m.p.: 54–55° C.

EXAMPLE 2

SYNTHESIS OF CMI-546

Part 1. 3-Benzyloxy-4-Hydroxy Benzaldehyde
(Scheme 1 above; 2)

To a mixture of 3,4-dihydroxy benzaldehyde (40.80 gms, 0.29 mol) and ethanolic potassium hydroxide (2 N, 320 mL) benzylchloride (37.54 g, 0.29 mol) was added slowly at room temperature. The reaction mixture was stirred overnight under nitrogen. The ethanol was removed on rotavapour and remaining solution treated with ice water. For removal of dibenzyl ether alkaline solution was extracted with diethyl ether (500 ml). Then the aqueous layer was acidified with concentrated hydrochloric acid and extracted thrice with ethyl acetate (800 ml). The organic layer was dried ($Na_2SO_4$), filtered and concentrated. The crude product was purified on silica gel column using EtOAc:light petroleum (1:9) as eluent to give 3-bezyloxy-4-hydroxy benzaldehyde (19.80 g, 29%). TLC: Ethyl acetate:light petroleum (1:4), $R_f$=0.3; m.p: 109–111° C.; $^1$H NMR (CDCl$_3$, 200 MHz): δ 5.06 (s, 2H), 6.39 (s,1H), 6.95 (d, J=8.0 Hz, 1H), 7.1–7.4 (m, 7H) and 9.57 (s, 1H).

Part 2. 3-Benzyloxy-4-hydroxy-5-Iodo Benzaldehyde (Scheme 1 above; 3)

To a mixture of 3-Benzyloxy-4-hydroxy benzaldehyde (15 g, 0.065 mol) and Iodine (17.54 g, 0.13 mol) was added 3.2% NaOH solution (150 ml). The reaction mixture was stirred at 75–80° C. for 8 h. The reaction mixture was cooled to room temperature and concentrated hydrochloric acid was added and the solid was filtered. Then the compound was recrystalized with isopropanol. The solid was filtered and dried to give 3-benzyloxy-4hydroxy-5-Iodo benzaldehyde (18.40 g, 79%). TLC: Ethyl acetate:light petroleum (2:5), $R_f$=0.4; $^1$H NMR (CDCl$_3$, 200 MHz): δ 5.20 (s, 2H), 7.23–7.45 (m, 6H), 7.8 (d, J=1.42 Hz, 1H), 9.73 (s,1H).

Part 3. 3-Benzyloxy-4-propoxy-5-Iodo benzaldehyde (Scheme 1 above; 4)

To a mixture of 3-benzyloxy-4-hydroxy-5-iodo benzaldehyde (23.1 g, 0.065 mol) and potassium carbonate (11.70 g, 0.084 mol) in DMF (55 ml) was added 1-bromo propane (12.03 g, 0.09 mol). The reaction mixture was stirred at 75–80° C. for 12 h. The reaction mixture was cooled to room temperature, diluted with water and extracted with ether (480 ml). The ether layer was dried Na$_2$SO$_4$), filtered and concentrated. The crude product was purified on silica gel column using (1:18) EtOAc: light petroleum as eluent to give the 3-benzyloxy-4-propoxy-5-Iodo benzaldehyde (21.4 g, 83%). TLC: Ethyl acetate:light petroleum (1:9), $R_f$=0.5; $^1$H NMR (CDCl$_3$, 200 MHz): δ 1.03 (t, J=7.21 Hz, 3H), 1.75 (m, 2H), 4.05 (t, J=6.66 Hz, 2H), 5.15 (s, 2H), 7.3–7.45 (m, 6H), 7.83 (d, J=1.54 Hz, 1H), 9.79 (s, 1H).

Part 4. Ethyl-4-(3-benzyloxy 4-propoxy-5-iodophenyl)-4-oxo-1-butanoate (Scheme 1 above; 5)

To a solution of 3-benzyloxy-4-propoxy-5-iodo benzaldehyde (25.5 g, 0.064 mol) in DMF (155 ml) was added sodium cyanide (0.78 g, 0.016 mol) and stirred at room temperature for 45 min under nitrogen atmosphere. Ethyl acrylate (5.21 g, 0.057 mol) in DMF (30 ml) was added slowly and stirred at room temperature for 30–40 mints. Ethyl acetate (185 ml) and 15% NaCl solution were added to the reaction mixture and the two layers were separated. The aqueous phase was extracted with ethyl acetate (250 ml). The combined organic extracts were washed with saturated aqueous NaHCO$_3$ (125 ml) followed by 5% aqueous NaCl (180 ml). The ethyl acetate layer was dried Na$_2$SO$_4$), filtered and concentrated. The crude product was purified on silica gel column using ethyl acetate:light petroleum (1:12) as eluent to give ethyl-4-(3-benzyloxy 4-propoxy-5-iodophenyl)-4-oxo-1-butanoate as a syrup (23.80 g, 74%). TLC: Ethyl acetate:light petroleum (1:9), $R_f$=0.4; $^1$H NMR (CDCl$_3$, 200 MHz): δ 1.05 (t, J=7.4 Hz, 3H), 1.3 (t, J=6.97 Hz, 3H) 1.78 (m, 2H), 2.7 (t, J=6.5 Hz, 2H), 3.1 (t, J=6.5 Hz, 2H), 4.06 (t, J=5.6 Hz, 2H), 4.18(q, J=7.1 Hz, 2H), 5.12 (s, 2H), 7.33–7.43 (m, 5H), 7.58 (d, J=1.62 Hz, 1H), 7.97 (d, J=1.62 Hz, 1H); IR (neat): 2970, 2930, 1735, 1690, 1585, 1550 cm$^{-1}$

Part 5. 4-(3-benzyloxy-4-propoxy-5-iodophenyl) Butyrolactone (Scheme 1 above; 7)

To a stirring solution of ethyl-4-(3-benzyloxy 4-propoxy-5-Iodophenyl)-4-oxo-1-butanoate (15.8 g, 0.031 ml) in ethanol (80 ml) at 0° C., was added sodium borohydride (0.90 g, 0.023 mol) slowly. The reaction mixture stirred for 10–15 mins at 0° C. The ethanol was removed and water was added and extracted with ethyl acetate (300 ml) dried, filtered and concentrated. The crude containing hydroxyester 6 and lactone 7 were purified on silica gel column using (1:5) EtoAc:light petroleum. The mixture was dissolved in dichloromethane (60 ml); to it PTSA (catalytic, 680 mg) was added at 0° C. and stirred at room temperature over night under nitrogen atmosphere. The dichloromethane solution was washed with water and aqueous NaHCO$_3$ (50 ml), dried (Na$_2$SO$_4$), filtered and concentrated. The crude product was purified on silica gel column using EtOAc: light petroleum (1:5) to give 4-(3-benzyloxy-4-propoxy-5-Iodophenyl) butyrolactone (11.4 g, 79%). TLC: Ethyl acetate:light petroleum (1:3), $R_f$=0.25; $^1$H NMR: δ 1.03 (t, J=7.90 Hz, 3H), 1.75–1.90 (m, 2H), 2.0–2.3 (m, 1H), 2.45–2.65 (m,3H), 3.96 (t, J=6.04 Hz, 2H), 5.08 (s, 2H), 5.35 (t, J=6.97 Hz, 1H), 6.88 (d, J=1.62 Hz, 1H), 7.28 (d, J=1.62 Hz, 1H), 7.30–7.40 (m, 5H); EI Mass: 452 (M$^+$), IR (neat): 3070, 2960, 2895, 1760, 1600, 1585 cm$^{-1}$

Part 6. 4-(3-benzyloxy-4-propoxy-5-propylthiophenyl) Butyrolactone (Scheme 1 above; 8)

To a solution of 4-(3-benzyloxy-4-propoxy-5-Iodophenyl) butyrolactone (11.4 g, 0.025 mol) in DMF (60 ml) were added propyl disulfide (10.23 g, 0.068 mol) and copper powder (6.4 g, 0.10 mol). The reaction mixture was stirred at 100° C. for 24 h. The reaction mixture was cooled to room temperature and copper powder was filtered through celite and washed with ethyl acetate (80 ml). NH$_4$Cl: NH$_4$OH (9:1) solution (50 ml) was added and extracted with ethyl acetate (180 ml) dried (Na$_2$SO$_4$), filtered concentrated. The crude product was purified on silica gel column using (1:4) EtOAc: light petroleum to give 4-(3-benzyloxy-4-propoxy-5-propylthiophenyl) butyrolactone as syrup (8.75 g, 86%). TLC: Ethyl acetate:light petroleum (1:3), $R_f$=0.25; $^1$H NMR (CDCl$_3$, 200 MHz): δ 1.05 (q, J=6.81 Hz, 6H), 1.6–1.9 (m, 4H), 2.04–2.2 (m,1H), 2.52–2.65 (m, 3H), 2.85 (t, J=6.58 Hz, 2H), 3.97 (t, J=6.81 Hz, 2H), 5.08 (s, 2H), 5.4 (t, J=6.81 Hz, 1H), 6.7 (s, 1H), 6.75 (s, 1H), 7.3–7.45 (m, 5H); IR (neat): 2975, 2945, 2880, 1745, 1590 cm$^{-1}$ EI Mass: 400 (M$^+$).

Part 7. 4-(3-benzyloxy-4-propoxy-5-propylsulfonylphenyl) butyrolactone (Scheme 1 above; 9)

To a solution of 4-(3-benzyloxy-4-propoxy-5-propylthiophenyl) butyrolactone (8.75 g, 0.021 mol) in dry dichloromethane (80 ml) was added m-chloroperbenzoic acid (9.43 g, 0.054 mol) slowly at 0° C. Then the reaction mixture was stirred at room temperature for 2 h. Then the solid was filtered through celite and washed with dichloromethane (100 ml). The organic layer was washed with saturated sodium bicarbonate solution followed by brine, dried (Na$_2$SO$_4$), filtered and concentrated. The crude compound was purified on silica gel column using EtOAc: light petroleum (2:3) as elutent to give 4-(3-benzyloxy-4-propoxy 5-propylsulfonylphenyl) butyrolactone as solid (6.9 g, 73%). m.p. 95–96° C.; TLC: Ethyl acetate:light petroleum (2:3), $R_f$=0.3; $^1$H NMR (CDCl$_3$, 200 MHz): δ 1.0 (q, J=6.45 Hz, 6H), 1.62–1.9 (m, 4H), 2.05–2.3 (m, 1H), 2.45–2.75 (m, 3H), 3.35 (t, J=6.02 Hz, 2H), 4.14 (t, J=6.45 Hz, 2H), 5.13 (s, 2H), 5.45 (m, 1H), 7.27 (d, J=1.42 Hz, 1H), 7.33–7.45 (m, 6H); IR (neat): 3010, 2930, 1765, 1600, 1490, 1460 cm$^{-1}$ EI Mass: 432 (M$^+$).

Part 8. 2-hydroxy-5-(3-benzyloxy-4-propoxy-5-propylsulfonylphenyl) Tetrahydrofuran (Scheme 1 above; 10)

To a solution of 4-(3-benzyloxy-4-propoxy-5-propylsulfonylphenyl) butyrolactone (6.90 g, 0.015 mol) in dry toluene (65 ml) at −78° C. was added 0.9 M toluene solution of DIBAL-H (3.40 g, 26.61 ml) dropwise at −78° C. and stirred for 1 h. Upon completion, the reaction was quenched by adding methanol (7 ml) at −78° C. The mixture was warmed to −20° C. followed by the addition of saturated sodium potassium tartarate solution while maintaining the temperature between −10° C. and 0° C. The mixture was stirred at 0° C. for 1 h. Then the two phases were separated, the aqueous layer was extracted with ethyl acetate and the combined organic layer was washed with water followed by brine, dried ($Na_2SO_4$), filtered and concentrated. The crude 2-hydroxy-5-(3-benzyloxy-4-propoxy-5-propylsulfonylphenyl) tetrahydrofuran (6.86 g) was used for the next step without further purification (99%). TLC: Acetone:benzene (1:9), $R_f$=0.33; $^1$H NMR($CDCl_3$, 200 MHz): δ 1.03 (m, 6H), 1.65–2.15 (m, 7H), 2.3–2.6 (m, 1H), 3.35 (m, 2H ), 4.15 (t, J=6.45 Hz, 2H), 4.98 (apparent t, J=6.97 Hz, 0.5H), 5.18 (t, J=6.51 Hz, 0.5H), 5.15 (2s, 2H), 5.6, 5.75 (brs, 1H), 7.1–7.22 (m, 1H), 7.3–7.48 (m, 6H). FAB Mass: 434 ($M^+$).

Part 9. 2-(o-t-butyldimethylsilyl)-5-(3-benzyloxy-4-propoxy-5-propylsulfonylphenyl) Tetrahydrofuran (Scheme 1 above; 11)

To a solution of 2hydroxy-5-(3-benzyloxy-4-propoxy-5-propylsulfonylphenyl) tetrahydrofuran (6.86 g, 0.015 mol) in dry DMF (300 ml) at 25° C. under nitrogen was added imidazole (2.36 g, 0.034 mol) followed by t-butyl dimethyl silyl chloride (2.62 g, 0.017 mol). The mixture was stirred at 25° C., under nitrogen for 3.5 h. After completion of the reaction ethyl acetate and water were added, extracted with ethyl acetate (120 ml). The combined organic layer was washed with brine, dried ($Na_2SO_4$), filtered and concentrated. The crude products were purified on silica gel column using EtOAc: light petroleum (1:15) as eluent to give the 2:1 mixture of 2-(o-t-butyldimethylsilyl)-5-(3-benzyloxy-4-propoxy-5-propylsulfonylphenyl) tetrahydrofuran (8.45 g, 97%); TLC: Ethyl acetate:light petroleum (1:9), $R_f$=0.4, 0.5; $^1$H NMR ($CDCl_3$, 200 MHz): δ 0.13 (m, 6H), 0.9 (s, 9H), 1.0 (q, J=6.59 Hz, 6H), 1.6–2.1 (m, 7H), 2.5 (m, 1H), 3.35 (m, 2H), 4.13 (t, J=5.90 Hz, 2H), 5.15 (m, 3H), 5.68 (bd, 1H), 7.16 (d, J=1.36 Hz, 1H), 7.32–7.46 (m, 6H). FAB Mass: 491 ($M^+$-t-bu).

Part 10. Preparation of (3,4,5-Trimethoxyphenyl) Magnesium Bromide

Magnesium (0.82 g, 33.74 mmol) was taken in flame dried 100 ml two necked flask and dry TEF (20 ml) was added. Then the dibromo ethane (0.1 ml) and trimethoxy bromobenzene (0.3 g, 1.20 mmol) were added at room temperature and stirred for 20 mins. The reaction initiates as indicated by temperature rise. The remaining bromide/THF (8.8 g, 35.48 mmol) in THF (20 ml) was added over 15 mints. After the addition was completed reaction mixture was stirred at 25° C. under nitrogen for 18 h. To the Grignard reagent at 0° C. was added a solution of dilithium tetrachlorocuprate (0.5 M, 0.76 ml, 0.38 mmol). The reaction was stirred at 0° C. for 15 mints and was used immediately for the coupling reaction.

Part 11. (±)-trans-2-(3-Benzyloxy-4-propoxy-5-propylsulfonylphenyl)-5-(3,4,5-trimethoxyphenyl) Tetrahydrofuran (Scheme 1 above; 12)

To a solution of 2-(o-t-butyldimethylsilyl)-5-(3-benzyloxy-4-propoxy-5-propylsulfonylphenyl) tetrahydrofuran (8.45 g, 15.41 mmol) in dichloromethane (80 ml) was added TMSBr (2.59 g, 2.20 ml, 16.96 mmol) at −78° C. under nitrogen atmosphere. The mixture was stirred at −78° C., for 1.5. The grignard/$Li_2CuCl_4$ mixture was transferred via cannula over 10 mints to the reaction vessel containing bromoether. The mixture was stirred for 1 h at −78° C. and quenched with 10:1 saturated $NH_4Cl/NH_4OH$ (50 ml) and water was added to dissolve the salts. The mixture was stirred for 30 mints without external cooling. The organic layer was removed and aqueous phase was extracted with ethyl acetate (150 ml). The combined organic layer was washed with brine (100 ml), dried ($Na_2SO_4$), filtered and concentrated. The crude product was purified on silica gel column using EtOAc:light petroleum (1:5) as eluent to give (±)-trans-2-(3-benzyloxy-4-propoxy-5-propylsulfonylphenyl)-5-(3,4,5-trimethoxyphenyl) tetrahydrofuran. The product contains some colour impurity at the same Rf value which was removed in the next step (6.48 g, 71%). TLC: Ethyl acetate:light petroleum (3:2), $R_f$=0.7; $^1$H NMR ($CDCl_3$, 200 MHz): δ 1.03 (q, J=6.97 Hz, 6H), 1.67–2.05 (m, 6H), 2.38–2.52 (m, 2H), 3.35 (t, J=7.90 Hz, 2H), 3.83 (s,3H), 3.88 (s, 6H), 4.14 (t, J=7.44 Hz, 2H), 5.08–5.27 (m, 4H), 6.57 (s, 2H), 7.3–7.48 (m, 7H); IR (neat): 2975, 2920, 2865, 1600, 1445 $cm^{-1}$ FAB Mass: 585 ($M^+$+1); HRMS: calculated. 585.253659; found. 585.252216.

Part 12. (±)-trans-2-(3-hydroxy-4-propoxy-5-propylsulfonylphenyl-5-(3,4,5-trimethoxyphenyl) Tetrahydrofuran (Scheme 1 above; 13)

To a solution of (±)-trans-2-(3-benzyloxy-4-propoxy-5-propylsulfonylphenyl)-5-(3,4,5-trimethoxyphenyl) tetrahydrofuran (6.35 g, 10.87 mol) in ethyl acetate (50 ml) was added 10% pd/c (0.80 g). The reaction mixture was stirred at room temperature under balloon pressure for 2 h. The Pd/C was filtered through celite and washed with ethyl acetate (80 ml). The filtrate was concentrated and the crude product was purified through silica gel column using Ethyl acetate:light petroleum (1:3) to give (±)-trans-2-(3-hydroxy-4-propoxy-5-propylsulfonylphenyl)-5-(3,4,5-trimethoxyphenyl tetrahydrofuran as a solid (3.30 g, 61%). TLC: Ethyl acetate:light petroleum (3:2), $R_f$=0.5 ; m.p. 115–117° C.; $^1$H NMR ($CDCl_3$, 200 MHz): δ 0.95 (t, J=7.72 Hz, 3H), 1.0 (t, J=6.81 Hz, 3H), 1.6–1.95 (m, 6H), 2.3–2.42 (m, 2H), 3.25 (m, 2H), 3.75 (s, 3H), 3.80 (s, 6H), 4.03 (t, J=6.12 Hz, 2H), 5.0–5.13 (m, 2H), 6.28 (s, 1H), 6.5 (s, 2H), 7.18 (d, J=1.54 Hz, 1H), 7.34 (d, J=1.54 Hz, 1H); IR (neat): 3400, 2975, 2945, 2860, 1725, 1540, 1490, 1440 $cm^{-1}$. FAB Mass: 495 ($M^+$), HRMS:calculated 0.495.205265; found. 495.207215.

Part 13. (±)trans-2-[3-(3-pthalimidopropoxy)-4-propoxy-5-propylsulfonyl phenyl]-5-(3,4,5-trimethoxyphenyl) Tetrahydrofuran (Scheme 1 above; 14)

To a solution of (±)-trans-2-(3-hydroxy-4-propoxy-5-propylsulfonylphenyl)-5-(3,4,5-trimethoxyphenyl) tetrahydrofuran (2.80 g, 5.66 mol) in acetone (40 ml) were added potassium carbonate (1.01 g, 7.36 mol) and N-(3-bromopropyl) pthalimide (2.06 g, 8.50 mmol). The reaction mixture was refluxed for 16 h. The reaction mixture was cooled to room temperature and acetone was removed, water was added and extracted with ethyl acetate (120 ml), dried ($Na_2SO_4$), filtered and concentrated. The crude product was purified on silica gel column using Ethyl acetate:light petroleum (2:5) to give (±)-trans-2-[3-(3-pthalimidopropoxy)-4-propoxy-5-propylsulfonyl phenyl]-5-(3,4,5- trimethoxyphenyl) tetrahydrofuran as solid (3.71 g, 94%). TLC: Ethyl acetate:light petroleum (2:1), $R_f$=0.5 ; m.p. 195–196° C. $^1$H NMR (CDCl$_3$, 200 MHz): δ 1.05 (t, J=7.14 Hz, 3H), 1.08 (t, J=6.66 Hz, 3H), 1.68–2.06 (m, 6H), 2.2–2.3 (m, 2H), 2.4–2.55 (m, 2H), 3.35 (m, 2H), 3.83 (s, 3H), 3.9 (s, 6H), 3.95 (t, J=6.6 Hz, 2H), 4.15 (t, J=6.13 Hz, 4H), 5.2 (m, 2H), 6.58 (s, 2H), 7.23 (d, J=1.5 Hz, 1H), 7.45 (d, J=1.51 Hz, 1H), 7.7 (m, 2H), 7.85 (m, 2H); IR (neat): 3010, 2975, 1775, 1715, 1600, 1490, 1380 cm$^{-1}$ FAB Mass: 681(M$^+$); HRMS: calculated. 681.260769; found. 681.265005.

Part 14. (±)-trans-2-[3-(3-aminopropoxy)-4-propoxy-5-propylsulfonylphenyl]-5-(3,4,5-trimethoxyphenyl) Tetrahydrofuran (Scheme 1 above; 15)

To a solution of (±)-trans-2-[3-(3-pthalinidopropoxy)-4-propoxy-5-propylsulfonyl phenyl]-5-(3,4,5-trimethoxyphenyl) tetrahydrofuran (3.71 g, 5.44 mmol), in ethanol (60 ml) was added hydrazine monohydrate (0.95 g, 19.06 mmol). The reaction mixture was refluxed for 10 h, then the reaction mixture was cooled to room temperature. The ethanol was removed, water was added and extracted with chloroform (120 ml). Organic layer was washed with brine, dried (Na$_2$SO$_4$), filtered and concentrated. The crude (±)-trans-2-[3-(3-aminopropoxy)-4-propoxy-5-propylsulfonylphenyl]-5-(3,4,5-trimethoxyphenyl)-tetrahydrofuran was used for further reaction without purification (3.43 g). TLC: Methanol:chloroform (1:9), $R_f$=0.3; $^1$H NMR (CDCl$_3$, 200 MHz): δ 0.95–1.02 (m, 6H), 1.6–2.0 (m, 8H), 2.35–2.50 (m, 2H), 2.90 (t, J=6.8 Hz, 2H), 3.3 (m, 2H), 3.78 (s, 3H), 3.82 (s, 6H), 4.08 (m, 4H), 5.05–5.2 (m, 2H), 6.55 (s, 2H), 7.20 (d, J=1.36 Hz, 1H), 7.40 (d, J=1.36 Hz, 1H).

Part 15. (±)-trans-2-[3-(3-(N$^1$-butyl-N$^1$-benzyloxyureidyl)propoxy)-4-propoxy-5-propylsulfonyl phenyl]-5-(3,4,5-trimethoxyphenyl) Tetrahydrofuran (Scheme 1 above; 16)

To a solution of (±)-trans-2-[3-(3-aminopropoxy)-4-propoxy-5-propylsulfonylphenyl]-5-(3,4,5-trimethoxyphenyl) tetrahydrofuran (3.43 g, 6.22 mmol) in dichloromethane (30 ml) was added triphosgene (0.92 g, 3.11 mol) and triethylamine (1.73 ml, 12.44 ml) at room temperature. The reaction mixture was refluxed for 2 h and then cooled with an ice bath to this cold solution was added butyl N-(O-benzyl)amine (2.78 g, 15.56 mmol) and triethylamine (3.45 ml, 24.84 mmol). The reaction mixture was stirred at room temperature for 3 h and then quenched with water and extracted with chloroform (120 ml). Organic layer was washed with brine, dried (Na$_2$SO$_4$), filtered and concentrated. The crude product was purified on silica gel column using ethyl EtOAc:light petroleum (1:3) to give (±)-trans-2-[3-(3-(N$^1$-butyl-N$^1$-benzyloxyureidyl)propoxy)-4-propoxy-5-propylsulfonyl phenyl]-5-(3,4,5-trimethoxy phenyl) tetrahydrofuran as syrup (3.32 g, 80%). TLC: Ethyl acetate:light petroleum (1:1), $R_f$=0.5; $^1$H NMR (CDCl$_3$, 200 MHz): δ 0.83–1.08 (m, 9H), 1.2–1.4 (m, 2H), 1.5–2.05 (m,10H), 2.23–2.5 (m, 2H), 3.25–3.4 (m, 4H), 3.48 (t, J=6.81 Hz), 2H), 3.8 (s, 3H), 3.85 (s, 6H), 3.94 (t, J=6.12 Hz, 2H), 4.08 (t, J=6.35 Hz, 2H), 4.72 (t, J=6.5 Hz, 2H), 5.2 (m, 2H), 5.74 (t, J=4.54 Hz, 1H), 6.58 (s, 2H), 7.2 (d, J=1.36 Hz, 1H), 7.3 (s, 5H), 7.48 (d, J=1.36 Hz, 1H); IR (neat): 3440, 2960, 2880, 1685, 1660, 1500, 1472 cm$^{-1}$; FAB Mass: 757 (M$^+$); HRMS: calculated. 757.373393; found. 757.372186.

Part 16. (±)-trans-2-[3-(3-(N$^1$-butyl-N$^1$-hydroxyureidyl)propoxy)-4-propoxy-5-propylsulfonyl phenyl]-5-(3,4,5-trimethoxy phenyl) Tetrahydrofuran (CMI-546)

To a solution of (±)-trans-2-[3-(3-N$^1$-butyl-N$^1$-benzyloxyureidyl)propoxy)-4-propoxy-5-propylsulfonyl phenyl]-5-(3,4,5-trimethoxyphenyl) tetrahydrofuran (3.10 g, 4.10 mmol) in ethyl acetate (15 ml) was added 10% pd/c (465 mg). The reaction mixture was stirred at room temperature under balloon pressure for 6 h. Then pd/c was filtered and washed with ethyl acetate (80 ml). The filtrate was concentrated. The crude product was purified on silica gel column using EtOAc:light petroleum (3:2) to give (±)-trans-2-[3-(3-N$^1$-butyl-N$^1$-hydroxyureidyl)propoxy)-4-propoxy-5-propylsulfonylphenyl]-5-(3,4,5-trimethoxy phenyl) tetrahydrofuran as solid (2.07 g, 75%). TLC: Ethyl acetate:light petroleum (3:1), $R_f$=0.3; m.p. 102–104° C. $^1$H NMR (CDCl$_3$, 200 MHz) δ 0.83 (t, J=6.97 Hz, 3H), 0.95 (q, J=6.97 Hz,6H), 1.22 (sextet, 2H), 1.4–1.53 (m, 2H), 1.6–2.05 (m, 8H), 2.4 (m, 2H), 3.28–3.4 (m, 6H), 3.79 (s, 3H), 3.83 (s, 6H), 4.08 (t, J=6.04 Hz, 4H), 5.17 (m, 2H), 6.03 (t, J=5.11 Hz, 1H); 6.54 (s, 2M), 7.0 (broadpeak, 1H), 7.2 (d, J=1.40 Hz,1H), 7.42 (d, J=1.40 Hz, 1H); IR (neat): 3410, 3230, 2945, 2830, 1650, 1585, 1520, 1460 cm$^{-1}$. FAB Mass: 667(M$^+$), HRMS: calculated. 667.326443, found. 667.326443. Purity of the compound 98.25%. HPLC: 70% methanol in water, column: ODS, flowrate 1.0 ml/min, WV: 225 nm. Chiral HPLC conditions: The two enantiomers (1:1) were separated on chiral HPLC: 40% isopropanol in n-hexane. Column: Chiracel (OD): Flow rate: 2.0 ml/min UV: 225 nm. Optical rotation: Compound 1 $[α]_D$=24.4 (C 1, CHCl$_3$), compound 2 $[α]_D$=−31.60 (C 1, CHCl$_3$).

EXAMPLE 3

Part. 1. 3-methoxy-4-benzyloxy Benzaldehyde (Scheme 2 above, 2)

To a solution of 3-methoxy-4-hydroxy benzaldehyde (10.0 g; 64.9 mmol) in dry acetone (80 ml), potassium carbonate (17.9 gm, 129.8 mmol) and BnBr (11.5 ml, 97.30 mmol) were added and stirred in room temperature for 18 hours. Potassium carbonate was filtered, acetone concentrated and the residue purified on silica gel to give the title compound as a crystalline solid 14 gm, 88%). $^1$H NMR (CDCl$_3$, 200 MHz): δ 3.9 (s, 3H), 5.2 (s, 2H), 6.95 (d, J=8.37 HZ, 1H), 7.4 (m, 7H), 9.8 (s, 1H); Mass (m/z): M$^+$242, mp: 58° C.

Part 2. 1-(3-methoxy-4-benzyloxyphenyl)-2-yne-1-propanol (Scheme 2 above, 3)

To a stirring solution of magnesium (1.19 g, 49.5 mmol) in THF (10 ml) was added ethyl bromide (3.7 ml, 49.5 mmol) under nitrogen at room temperature. After the dissolution of the magnesium, acetylene gas was bubbled through the reaction mixture at 0° C. for 20 minutes. compound (2) (4.0 g; 16.5 mmol) in THF was added. The reaction was (monitored by TLC) completed in 30 minutes at which time saturated NH$_4$Cl solution was added. THF was removed, the residue was extracted with diethyl ether, dried and concentrated. The residue was purified on silica gel to give title compound as a pale yellow solid (68%). $^1$H NMR (CDCl$_3$, 200 MHz): δ 2.0 (brd, 1H), 2.6 (d, J=1.39 Hz, 1H), 3.9 (s, 3H), 5.15 (s, 2H), 5.35 (brd, 1H), 6.82 (d, J=8.37 Hz, 1H), 7.0 (dd, J=8.37 Hz, J=1.39 Hz, 1H), 7.1 (d, J=1.39 Hz, 1H), 7,35 (m, 5H); Mass (m/z): M$^+$268; mp: 83–85° C.

Part 3. 1-(3-methoxy-4-benzyloxyphenyl)-4-(3,4,5-trimethoxyphenyl)-2-yne-1,4-butanediol (Scheme 2 above, 4)

To a stirring solution of ethyl magnesium bromide (prepared from 0.8 g of magnesium and 3.7 g of ethyl bromide) in THF, compound (3) (3.0 g, 11.2 mmol) was added and then reaction heated at 60° C. for 1 hour. The reaction mixture was allowed to attain room temperature and then 3,4,5-trimethoxybenzaldehyde (2.2 g, 11.2 mmol) was added. After stirring 1.5 hours at room temperature, saturated $NH_4Cl$ solution was added followed by removal of THF under reduced pressure. The residue was extracted with ether, dried over $Na_2SO^4$ and concentrated. The crude product was purified on silica gel to yield as a yellow solid (65%). $^1H$ NMR ($CDCl_3$, 200 MHz): δ 3.8 (s, 6H), 3.85 (s, 6H), 5.15 (s, 2H), 5.42 (brs, 2H), 6.73 (s, 2H), 6.8 (d, J=6.9 Hz, 1H), 7.0 (dd, J=6.97 Hz, J=m 1.39 Hz, 1H), 7.06 (d, J=1.39 Hz, 1H), 7.4 (m, 5H); Mass (m/z): $M^+$ 464; mp: 110° C.

Part 5. 2-(3-methoxy-4-hydroxyphenyl)-5-(3,4,5-trimethoxyphenyl)tetrahydrofuran (Scheme 2 above, 6)

A solution of compound (4) (5.0 g, 10.8 mmol), Raney nickel (12.5 ml of settled material) in ethanol was hydrogenated at normal temperature and pressure for 2 hours. Catalyst was filtered, ethanol concentrated, the residue purified on silica gel to yield the title compound (5), which was taken further to the next reaction.

Compound (5) (0.94 gm, 2.5 mmol) and trifluoroacetic acid (1 ml) in chloroform (20 ml) was stirred at 0° C. for 2 hours at room temperature. The reaction was diluted with dichloromethane, washed with 10% NaOH solution, water and saturated NaCl solution, dried over $Na_2SO_4$ and evaporated in vacuo to obtain the compound (6) as a cis-trans mixture (0.37 gm, 43%). $^1H$ NMR ($CDCl_3$, 200 MHz): δ 2.0 (m, 2H), 2.4 (m, 2H), 3.85 (s, 3H), 3.87 (s, 3H), 3.93 (s, 6H), 5.0 (t, J=6.81 Hz, 1H), 5.15 (m, 1H), 6.6 (s, 2H), 6.86 (d, J=4.54 Hz, 2H), 6.94 (s, 1H); Mass (m/z): $M^+$ 360.

Parts 6–9. Cis/trans-2-(3',4',5'-Trimethoxyphenyl)-5-[3"-iodo-5"-methoxy-4-(2-p-chlorothiophenylethoxy)phenyl]tetrahydrofuran (Scheme 2, 7–10)

Intermediate compounds 7, 8, 9, and 10 can be made along lines shown in Scheme 2 and in accord with standard synthetic techniques known in the field. In particular, the production of the compound 10 from reaction of intermediate compounds 8 and 9 can be achieved by performing reactions along lines shown for the transformation of intermediate compounds 204, 205 and 206 (see FIG. 2a). The compound 10 is essentially the same as intermediate compound 111 as shown in FIG. 1b (see also Example 1). As provided in FIG. 1b and the examples, that compound 111 can be reacted along lines shown in FIGS. 1b–1c to produce essentially pure crystalline CMI-392.

EXAMPLE 4

Synthesis of CMI-392 Using Aspirin as Starting Material

Methyl salicylate (Aspirin, FIG. 2a, 201) was heated with a Friedel-Crafts catalyst such as AIC13 to give Fries rearrangement product (202). Methylation of 202 using dimethyl sulfate in presence of anhydrous potassium carbonate furnished methyl ester (203), which was then reacted with iodine under basic condition to yield 204. Aromatic substitution of the iodide by methoxy group followed by O-alkylation using 1–2 dibromoethane gave 206. Compound 206 was treated with a mild base followed by p-chlorothiophenol to furnish 207, which was then reacted with paraformaldehyde and suitable amine hydrochloride such as dimethylamine HCI, in appropriate solvent such as isopropanol to yield Mannich salt (208) on heating. Compound 208 was converted to the quaternary ammonium salt with methyl iodide which on heating was converted to enone 209. Catalytic coupling of the enone (209) and trimethoxy benzaldehyde (108) in DMF furnished diketone 210. Reduction of the diketone (210) with a suitable reducing agent such as NaBH4 followed by acid catalysed cyclization gave substituted tetrahydrofuran, 211. Treatment of the separated bans isomer of the substituted tetrahydrofuran, (212) with ammonia in methanol and subsequent reduction furnished amine 213. The amine (213) on reaction with p-nitrophenyl chloroformate, and N-methylLydroxylamine in the presence of a base such as triethyl amine furnished CMI-392. CMI-392 was then crystallized in isopropyl alcohol.

What is claimed is:

1. A method for preparing a di-aryl tetrahydrofuran, comprising:
    a) reacting with a Grignard reagent a compound that has a carbon substituted by an acetylene group, an aryl group, and a hydroxyl group,
    b) saturating the acetylene moiety of the reaction product of step a); and
    c) cyclizing the reaction product of step b) to provide the di-aryl tetrahydrofuran.

2. The method of claim 1, wherein the acetylene group of step a) is a primary acetylene group and the aryl group is an optionally substituted phenyl.

3. The method of claim 1, wherein the acetylene moiety is hydrogenated in step b).

4. The method of claim 1, wherein the Grignard reagent is ethylmagnesium bromide.

5. The method of claim 1, wherein the di-aryl tetrahydrofuran formed in the method is further reacted to add a hydroxyl group to at least one of the aryl rings, the hydroxyl group being reacted with a di-haloalkyl compound to form an alkoxy group on the aryl ring.

6. The method of claim 5, wherein the compound produced in the method is further reacted with a substituted mercaptobenzene compound under conditions which add the substituted mercaptobenzene group to the alkoxy group.

7. The method of claim 6, wherein the compound formed in the method is further reacted under conditions sufficient to produce essentially pure crystalline CMI-392.

8. A method for preparing a diaryl substituted tetrahydrofuran compound comprising:
    (a) reacting methyl salicylate with a Friedel-Crafts catalyst to provide a Fries rearrangement compound;
    (b) $C_{1-6}$-alkylating the acid group of the Fries rearrangement compound and $C_{1-6}$alkoxylating the resulting compound;
    (c) coupling a compound resulting from step (b) with an optionally substituted benzaldehyde to form a diaryl-substituted substituted 1–4-diketo-butane compound,:
    (d) reducing the diketo compound to provide a diaryl-substituted tetrahydrofuran.

* * * * *